US010390975B2

(12) United States Patent
Hugate

(10) Patent No.: US 10,390,975 B2
(45) Date of Patent: Aug. 27, 2019

(54) TRANSCUTANEOUS IMPLANT FOR SKELETAL ATTACHMENT OF EXTERNAL PROSTHETIC DEVICES

(71) Applicant: Zimmer, Inc., Warsaw, IN (US)

(72) Inventor: Ronald Hugate, Aurora, CO (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/241,180

(22) Filed: Aug. 19, 2016

(65) Prior Publication Data

US 2016/0354216 A1 Dec. 8, 2016

Related U.S. Application Data

(63) Continuation of application No. 14/023,161, filed on Sep. 10, 2013, now abandoned.
(Continued)

(51) Int. Cl.
*A61F 2/30* (2006.01)
*A61F 2/68* (2006.01)
(Continued)

(52) U.S. Cl.
CPC ............ *A61F 2/78* (2013.01); *A61F 2/2814* (2013.01); *A61F 2/30771* (2013.01);
(Continued)

(58) Field of Classification Search
CPC ...... A61F 2/2814; A61F 2/30744; A61F 2/78; A61F 2002/6872; A61F 2002/7887;
(Continued)

(56) References Cited

U.S. PATENT DOCUMENTS

| 3,947,897 A | 4/1976 | Owens |
| 4,143,426 A | 3/1979 | Hall et al. |

(Continued)

FOREIGN PATENT DOCUMENTS

| WO | WO-1996039202 A1 | 12/1996 | | |
| WO | WO 2008/092967 | * 11/2007 | ............... | A61F 2/28 |
| WO | WO-2013048589 A1 | 4/2013 | | |

OTHER PUBLICATIONS

Derwent Abstract and Google translation for WO2008/092967A1. Guirao, Cano Luis. Aug. 7, 2008.*

(Continued)

*Primary Examiner* — Christie L Bahena
(74) *Attorney, Agent, or Firm* — Schwegman Lundberg & Woessner, P.A.

(57) ABSTRACT

Provided herein are devices and methods for connecting a transcutaneous external prosthetic device to a bone, such as a bone of an amputee. The device is a two-piece transcutaneous implant device to provide reversible connection for ease of implantation, reliability, and relatively easy access for removal, while maximizing tissue ingrowth to reduce risk of infection and attendant adverse outcomes. The devices provided herein comprise a prosthetic interface and a bone anchor. A through-hole that traverses a longitudinal length of the prosthetic interface and at least a longitudinal portion of the bone anchor receives a fastener to reversibly connect the prosthetic interface to the bone anchor implanted in bone. A connector may connect to a failsafe element which, in turn, connects to an external prosthetic device.

20 Claims, 27 Drawing Sheets

Related U.S. Application Data

(60) Provisional application No. 61/820,264, filed on May 7, 2013, provisional application No. 61/698,866, filed on Sep. 10, 2012.

(51) Int. Cl.
*A61F 2/78* (2006.01)
*A61F 2/28* (2006.01)

(52) U.S. Cl.
CPC ............... *A61F 2002/30013* (2013.01); *A61F 2002/30028* (2013.01); *A61F 2002/3092* (2013.01); *A61F 2002/3093* (2013.01); *A61F 2002/30884* (2013.01); *A61F 2002/6845* (2013.01); *A61F 2002/7887* (2013.01)

(58) Field of Classification Search
CPC ........ A61F 2/30771; A61F 2002/30884; A61F 2002/3092; A61F 2002/3093; A61F 2002/30013; A61F 2002/30028
See application file for complete search history.

(56) References Cited

U.S. PATENT DOCUMENTS

| | | | |
|---|---|---|---|
| 4,158,895 | A | 6/1979 | Frosch et al. |
| 4,781,720 | A | 11/1988 | Sherva-Parker |
| 5,041,137 | A | 8/1991 | Nemoshkalov |
| 5,057,101 | A | 10/1991 | Dorr |
| 5,478,238 | A | 12/1995 | Gourtou et al. |
| 5,489,306 | A | 2/1996 | Gorski |
| 6,197,065 | B1 | 3/2001 | Martin et al. |
| 6,425,925 | B1 | 7/2002 | Grundei |
| 6,482,238 | B1 | 11/2002 | Grundei |
| 6,485,522 | B1 | 11/2002 | Grundei |
| 6,508,841 | B2 | 1/2003 | Martin et al. |
| 6,712,855 | B2 | 3/2004 | Martin et al. |
| 6,869,450 | B2 | 3/2005 | Grundei |
| 7,014,661 | B2 | 3/2006 | Blunn et al. |
| 7,018,420 | B2 | 3/2006 | Grundei |
| 7,141,073 | B2 | 11/2006 | May et al. |
| 7,323,013 | B2 | 1/2008 | McTighe et al. |
| 7,374,577 | B2 | 5/2008 | Kim et al. |
| 7,476,254 | B2 | 1/2009 | White et al. |
| 7,578,851 | B2 | 8/2009 | Dong et al. |
| 7,722,678 | B2 | 5/2010 | Brown et al. |
| 7,909,883 | B2 | 3/2011 | Sidebotham |
| 2002/0099449 | A1 | 7/2002 | Speitling |
| 2003/0109878 | A1 | 6/2003 | Grundei |
| 2003/0171825 | A1 | 9/2003 | Blunn et al. |
| 2003/0195636 | A1 | 10/2003 | Coop |
| 2004/0006396 | A1 | 1/2004 | Ricci et al. |
| 2004/0068324 | A1 | 4/2004 | Grundei |
| 2004/0133207 | A1* | 7/2004 | Abdou ............... A61B 17/7059 623/16.11 |
| 2005/0102038 | A1 | 5/2005 | Grundei |
| 2005/0119758 | A1 | 6/2005 | Alexander et al. |
| 2006/0041318 | A1 | 2/2006 | Shannon |
| 2007/0060891 | A1 | 3/2007 | Skiera et al. |
| 2007/0073412 | A1 | 3/2007 | Blunn et al. |
| 2008/0020349 | A1 | 1/2008 | Dricot |
| 2008/0058957 | A1 | 3/2008 | Newcombe et al. |
| 2008/0161938 | A1 | 7/2008 | Gramnas |
| 2008/0200995 | A1 | 8/2008 | Sidebotham |
| 2008/0288087 | A1 | 11/2008 | Bachus et al. |
| 2009/0005820 | A1 | 1/2009 | Bloebaum |
| 2009/0036908 | A1 | 2/2009 | Zokol et al. |
| 2009/0149966 | A1 | 6/2009 | Blunn et al. |
| 2009/0292368 | A1 | 11/2009 | Plowman et al. |
| 2011/0029002 | A1 | 2/2011 | Mann et al. |
| 2011/0190907 | A1 | 8/2011 | Porter et al. |
| 2012/0310371 | A1 | 12/2012 | Bachus et al. |
| 2013/0006356 | A1 | 1/2013 | Cook et al. |
| 2013/0195540 | A1 | 8/2013 | Wozencroft et al. |
| 2014/0081422 | A1 | 3/2014 | Hugate |
| 2014/0156022 | A1 | 6/2014 | Holt |
| 2014/0214177 | A1 | 7/2014 | Porter et al. |
| 2014/0228973 | A1 | 8/2014 | Porter |

OTHER PUBLICATIONS

"2012 Product Information: Prosthetics & Orthotics", ST&G USA Corporation. Brea, CA, (2012), 76 pgs.
"U.S. Appl. No. 14/023,161, Advisory Action dated Jul. 15, 2016", 4 pgs.
"U.S. Appl. No. 14/023,161, Final Office Action dated Apr. 22, 2016", 19 pgs.
"U.S. Appl. No. 14/023,161, Non Final Office Action dated Jul. 23, 2015", 18 pgs.
"U.S. Appl. No. 14/023,161, Preliminary Amendment filed Dec. 4, 2013", 9 pgs.
"U.S. Appl. No. 14/023,161, Response filed Jan. 21, 2016 to Non Final Office Action dated Jul. 23, 2015", 18 pgs.
"U.S. Appl. No. 14/023,161, Response filed Jun. 22, 2016 to Final Office Action dated Apr. 22, 2016", 15 pgs.
"U.S. Appl. No. 14/023,161, Response filed Jul. 10, 2015 to Restriction Requirement dated Mar. 12, 2015", 8 pgs.
"U.S. Appl. No. 14/023,161, Restriction Requirement dated Mar. 12, 2015", 7 pgs.
"C-Leg Prosthetic System: Instructions for Use (Qualified Personnel)", Otto Bock Healthcare Products. Kaiserstabe, Austria, (Mar. 3, 2012), 28 pgs.
"International Application Serial No. PCT/US2013/059029, International Search Report dated Dec. 20, 2013", 2 pgs.
"International Application Serial No. PCT/US2013/059029, Written Opinion dated Dec. 20, 2013", 9 pgs.
"Limb Salvage Product Portfolio", brochure, Biomet Orthopedics, Inc, (2009), 23 pgs.
"Medex: Quality Products for the Prosthesis Industry", Medex International, [Online]. Retrieved from the Internet: http://www.medexinternational.com/index.htm, (2012), 2 pgs.
"Osseointegration in skeletal Reconstruction and Rehabilitation", Journal of Rehabilitation Research & Development, vol. 38 No. 2, [Online]. Retrieved from the Internet: <http://www.rehab.research.va.gov/jour/01/38/2/brane382.htm>,accessed Jul. 29, 2011, (Mar./Apr. 2001), 8 pgs.
"People with Amputation Speak Out", The Limb Loss Research & Statistics Program Amputee Coalition of America. Knoxville, (2006), 1-14.
"Regenerex Porous Titanium Construct", brochure, Biomet Orthopedics, Inc, (2008), 7 pgs.
"The Osseotite® Implant, The Surface That Succeeds. Proven Performance and Predictable", brochure, Biomet 31 LLC, Inc., (2009), 8 pgs.
Bozkaya, et al., "Mechanics of the Tapered Interference Fit in Dental Implants", Journal of Biomechanics, (2003), 1649-1658.
Brahatheeswaran, Dhandayuthapani, "Polymeric Scaffolds in Tissue Engineering Application: A Review. International Journal of Polymer Science", (2011), 1-19.
Fitzpatrick, Noel, "Intraosseous Transcutaneous Amputation Prosthesis, an Alternative to Limb Amputation in Dogs and Cats", Society of Practising Veterinary Surgeons, SPVS Review, (2009), 2-5 pgs.
Fryar, et al., "Anthropometric reference data for children and adults United States 2007-2010", Vital and Health Statistics, (Oct. 2012), 1-40.
McDowell, et al., "Anthropometric Reference Data for Children and Adults; United States, 2003-2006", National Health Statistics Reports. No. 10, (2008), 1-48.
Sanders, Gloria, "Lower limb amputation: A guide to rehabilitation", (1988), p. 549.

* cited by examiner

A.

B.

501

A.

B.

C.

A.

B.

A.

B.

FIG. 28
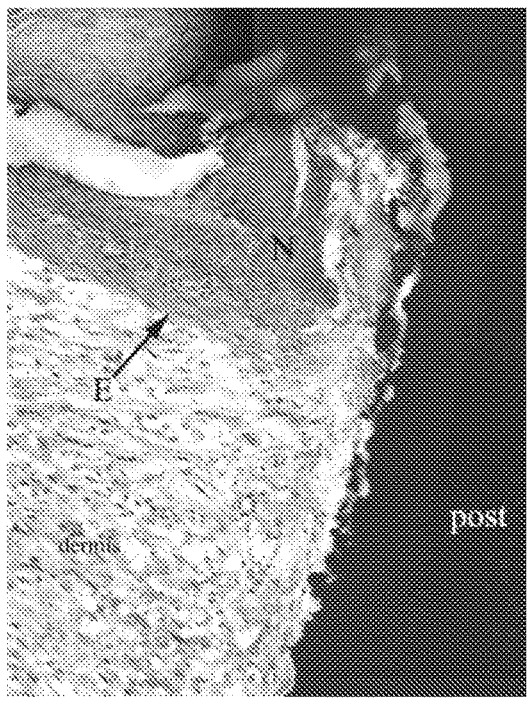
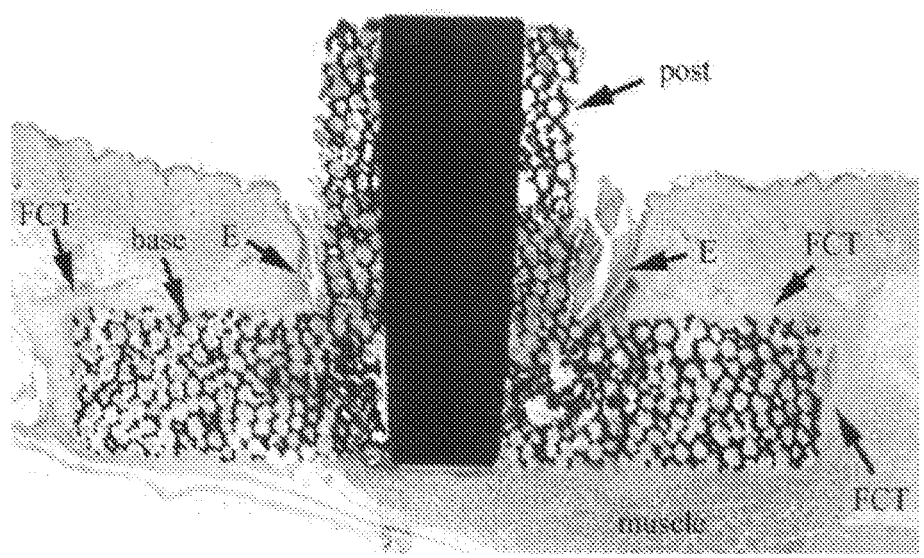
FIG. 29

TRANSCUTANEOUS IMPLANT FOR SKELETAL ATTACHMENT OF EXTERNAL PROSTHETIC DEVICES

CROSS-REFERENCE TO RELATED APPLICATIONS

This application is a continuation of U.S. patent application Ser. No. 14/023,161, filed Sep. 10, 2013, which claims benefit to U.S. Provisional Patent Application Nos. 61/698,866, filed Sep. 10, 2012 and 61/820,264, filed May 7, 2013, each of which are incorporated by reference to the extent not inconsistent herewith.

BACKGROUND OF THE INVENTION

Provided herein are devices and related methods for mechanically connecting an external prosthetic device to a user's skeleton via a transcutaneous implant.

Currently, amputees are most commonly fit with a socket interface prosthesis, with the socket contoured to fit the individual's residual limb. In this manner, the socket interface transmits forces from the appendicular skeleton through the soft tissues to the prosthesis. There are a number of significant disadvantages with such a configuration. First, skin breakdown is common as the soft-tissue/socket interface may create excessive pressure areas on the skin. The transmission of forces from the skeleton through the soft tissues is an energy inefficient process. Users having poorly fitting prostheses with this interface tend to lack proprioception, particularly as the standard prostheses do not tend to convey tactile feedback during use. Such feedback is valuable in dictating one's gait, cadence, etc., during movement and ambulation. Fluctuations in weight, muscular tone, edema, hydration, perspiration, level of activity and body habitus all affect the ability of the soft tissue/socket interface to function appropriately using standard socket-type prosthesis.

These problems are addressed herein by directly connecting the appendicular skeleton to the prosthesis via a transcutaneous implant. The implant is tailored to integrate with both bone and soft tissue while providing a means to directly attach a prosthesis to the skeleton. This avoids unwanted prosthetic physical interaction with soft tissue and improves energy transfer efficiency. Not only does the implant provide a durable mechanical construct, but the integration with both soft and a bone tissue provides beneficial biologic properties, including infection resistance.

SUMMARY OF THE INVENTION

Provided herein are implantable transcutaneous devices and related methods for connecting an external prosthetic device to bone. The implantable transcutaneous devices have a number of special design configurations to provide important functional benefit. For example, the implant is configured as a two-piece design with a bone anchor and a prosthetic interface, with the bone anchor configured for implantation in bone. The prosthetic interface, in contrast, is generally placed outside the bone passage, but reliably connected to the bone anchor in a transcutaneous manner such that a proximal portion is implanted within soft tissue at and beneath the skin, and a distal portion that is exposed to receive a prosthesis above the skin. A fastener can reliably connect the prosthetic interface to the bone anchor. Alternatively, female and male elements may be provided for a press-fit connection between the prosthetic interface and the bone anchor. Alternatively, the connection may comprise a combination of both fastening and press-fitting. In an embodiment, the connection between the bone anchor and the prosthetic interface can be distracted with the use of a distraction bolt to ease extraction of the components from bone. Such a connection configuration facilitates ease of extraction should the implant or a part of the implant need to be removed.

Furthermore, this two-piece design is compatible with failure load design, where mechanical failure is designed to occur at the prosthetic interface (outside of the body), such as at a failsafe, to minimize risk of damage to the bone-implanted bone anchor, the bone adjacent thereto, or other tissue or implanted component. In this manner, the damaged prosthetic portions may be removed and replaced without necessarily having to replace the implant, including the prosthetic interface or bone anchor.

In an embodiment, the invention is a transcutaneous device to anchor an external prosthetic device to a bone directly, the transcutaneous device comprising two separate components: a bone anchor configured for implantation into bone and a prosthetic interface for connecting an external prosthetic device to the bone anchor. A through-hole traverses a longitudinal length of the prosthetic interface and at least a longitudinal portion of the bone anchor. The through-hole is configured to receive a fastener that connects the prosthetic interface to the bone anchor, such as a bone anchor that has been implanted in bone. Alternatively, a distraction bolt may be inserted into the through-hole to aid in distraction and separation of the components should that become necessary. The prosthetic interface is configured for implantation external to bone and for soft tissue ingrowth and vascularization after implantation. The bone anchor, in contrast, is substantially or entirely implanted in bone.

In an aspect, the fastener provides physical contact between the prosthetic interface and the bone anchor defined by a contact region that corresponds to the bone surface, with the transcutaneous device above the bone corresponding to the prosthetic interface component and the device within the bone corresponding to the bone anchor. In an aspect, the contact region is shaped to provide a stable base for seating of the implant and for bony ingrowth medium to reduce or prevent infection. The contact region can include a step-off defined by different dimension of the prosthetic interface and bone anchor, such as a prosthetic connector diameter that is greater than the bone anchor diameter. The corresponding lip can then rest on the bone surface surrounding the bone anchor. Of course, the bone anchor may also include a portion that is not implanted in the bone, such as a male member, whose function is to reliably connect to the prosthetic interface portion. One example is a male member that is received by a passage within the prosthetic interface.

In an embodiment, the fastener is a bolt that secures the prosthetic interface to the bone anchor, wherein the bolt is dropped through the through-passage of the prosthetic interface to the through-passage of the bone anchor. In an aspect, the bolt is reversibly connected to the bone anchor, so that the prosthetic interface can be removed from the bone anchor by removing the bolt from the bone anchor. The reversible connection is by any means known in the art, such as an adhesive that may be removed or exposed to a physical or chemical signal that reduces adhesive bond strength, such as by electromagnetic radiation, temperature variation or chemical application that reduces adhesive bond strength. Another example of a reversible connection is a mechanical connection, such as threads on a bolt (external thread— male) and a threaded receptacle positioned in the bone anchor through-hole (internal thread—female).

The prosthetic interface may be further described by various constituent parts or elements. For example, the prosthetic interface has a distal end to connect to an external prosthetic device and a proximal end for connecting to the bone anchor and to rest against bone. A central portion extends between the distal and proximal ends. The central portion is a particularly significant aspect of the device and is designed to maximize soft-tissue ingrowth into the transcutaneous device. "Soft-tissue" refers to skin, subcutaneous tissue, muscle, blood vessels and other non-bony biological tissues that surround the prosthetic interface proximal end and central portion. To maximize soft-tissue ingrowth, the central portion of the prosthetic interface may have a shaped three-dimensional surface to maximize surface area for soft-tissue ingrowth and also to provide implant stability, specifically for the portion of the implant not within bone. This shaped three-dimensional surface is also referred to as a "shaped tissue ingrowth surface" and may refer to a surface that does not have any sharp edges or corners, thereby maximizing surface area available for tissue ingrowth and/or vascularization.

Extending from the distal portion of the shaped surface is a distal connecting element having at the end opposite to the shaped surface the distal end to which an external prosthetic can be attached. A suture ring for attaching skin to the prosthetic interface may be positioned within the distal connecting element Extending from the proximal portion of the shaped surface is the proximal connecting element having at the end opposite to the shaped surface the proximal end that can connect to the bone anchor and a bone surface in which the bone anchor is connected. The portion of the prosthetic interface that is subcutaneous, including the central portion and proximal end and selected portions thereof, may be a highly porous material, such as a foam metal, to act as a matrix for biologic ingrowth of various tissues, as desired.

In an aspect, the distal end of the prosthetic interface comprises a connector to mate the transcutaneous device to an external prosthetic device (or a failsafe element that is in turn connected to the external prosthetic device). The connector may be interchangeable so that the implant can be connected to any of a number of different external prosthetic systems. The connector is then selected based on the anticipated external prosthetic system selected for use in the individual patient. Examples of connectors include a pyramid-shaped connector or a male end Morse taper having a geometry that is cylindrical or oblong.

In this manner, the transcutaneous device may be configured to have an external prosthetic device-prosthetic interface failure load that is less than a bone anchor-bone failure load, or implant failure load, thereby minimizing or avoiding damage to the bone or the implant by a force exerted on an external prosthetic device that in the absence of the external prosthetic device-prosthetic interface failure load results in bone damage or implant failure. This ensures that when damaging force is encountered on the transcutaneous device, such as by the external prosthetic or by the force on the external prosthetic by the bone, the bone implanted portion or biological tissue is not damaged. Instead, the break point or damage point is external to the bone, such as at distal region of the prosthetic interface, including at the point of connection between the external prosthetic and the prosthetic interface. The failure point is configured to occur, in order of preference, at the external prosthetic, the prosthetic connector, and finally the bone anchor. In this manner, damage to the bone is avoided and likelihood of catastrophic implant or bone failure is minimized. A failsafe may operably connect the prosthetic interface to the prosthetic, wherein the failsafe ensures damaging forces are not transferred to the prosthetic interface or the bone anchor.

In an embodiment, the prosthetic interface further comprises a shaped tissue ingrowth surface configured for soft tissue ingrowth and vascularization. The shaped tissue ingrowth surface may be further described as having an apex region concentrically positioned on a distal portion of a central body outer surface, a rounded radial edge portion; and a convex outer-facing surface extending between the apex region and rounded radial edge portion. Such a shape maximizes surface area available for soft-tissue ingrowth and vascularization. In an aspect, the outer-facing surface is a distal surface and the inner-facing surface is a proximal surface. The inner-facing surface may be concave in shape, so that the inner surface and outer surface are somewhat parallel to each other, but shaped to increase contact surface area with the surrounding soft tissue without adversely impacting reliable implantation and unwanted movement. The shape may be characterized as umbrella-shaped, skirt-shaped or mushroom shaped.

In another embodiment, the shaped tissue ingrowth surface has a geometry that is substantially bulbous.

In an aspect, the shaped tissue ingrowth surface has a surface area that is selected depending on the anatomy in which the implant is to be implanted. Because the implant is configured for use with a wide range of anatomies that may span from bones within a finger to a thigh, as well as variations in the user such as age or animal type, the surface area is selected accordingly, such as a surface area that is between about 1 cm$^2$ and up to about 200 cm$^2$ or more, such as up to about 100 cm$^2$. Given the curved shape of the shaped surface, the invention optionally further comprises a structural enhancer element, such as a solid internal ring, to mechanically stabilize the shaped tissue ingrowth surface to the central body. The ring may be a solid metal material placed within the shaped surface that mechanically stabilizes the shaped surface that is made of a highly porous material. This configuration minimizes unwanted displacement and motions without adversely affecting tissue ingrowth. The configuration of the shaped surface ensures that both the distal and proximal facing surfaces, and the edge region there between, are accessible for soft tissue ingrowth. This shape, therefore, further reduces risk of infection and adverse outcomes post-implantation requiring implant removal and replacement.

In an embodiment, the prosthetic interface further comprises a suture ring positioned at the apex region of the tissue ingrowth surface to provide an anchoring point for skin upon implantation. In particular, the suture ring is positioned at an appropriate longitudinal distance along the prosthetic interface distal region and central portion to be substantially coincident with the skin location overlying the bone and sufficiently far from the distal end to which the external prosthetic interface connects so as to not interfere with the connection.

In an embodiment, a distal portion of the bone anchor and a proximal portion of the prosthetic interface are formed from or coated with a highly porous material to facilitate ingrowth of soft tissues and bone. In an aspect, the highly porous material comprises a ceramic, polymer, tantalum, titanium, or cobalt chrome steel. The highly porous material may have an initial porosity of up to 80% that subsequently decreases after implantation as tissue in growth occurs. In an aspect, the implant is formed from a solid metal core with foam coating in the regions where biological tissue ingrowth is desired. In an aspect, the pores are interconnected pores. Such a configuration enhances mechanical characteristics, while still taking advantage of the biological properties of the surrounding tissue, allowing the biologic tissues to more thoroughly permeate the pores. In an aspect, the target tissue is soft tissue for the prosthetic interface and bone for the bone anchor. The highly porous material has a pore density and/or pore size selected to the desired target tissue. For example, target tissue that is bone generally has a pore size that is smaller than for target tissue that is soft tissue. In this aspect, the porosity may vary with position, such as pore size that varies as the implant traverses skin, epidermal layers, muscle, highly vascularized areas, and bone. In an aspect, the highly porous material may contain antibiotics, anti-infectious chemicals, and/or morphogenic proteins to reduce the risk of deep infection as well as to help facilitate and steer the differentiation of tissues that permeate the implant. In an aspect, the highly porous material comprises tantalum with dodecahedral interconnecting pores, having a porosity selected from a range that is greater than 70% and less than 90%, and an average pore diameter that is selected from a range that is greater than 150 µm and less than 700 µm.

In an aspect, the proximal portion of the prosthetic interface connects to the distal portion of the bone anchor at a step-off region. In this manner, the step-off region can function as a base against which the bone outer surface rests, imparting vertical stability, with the portion of the transplant above the bone corresponding to the prosthetic interface, and the portion situated below the bone surface the bone anchor. A fastener that connects the prosthetic interface to the bone anchor traverses both the soft tissue and the bone. In an aspect, the proximal portion of the prosthetic interface and the distal portion of the bone anchor have a defined outer dimension, such as for a cylinder or ellipse, and the proximal portion outer diameter is greater than the distal portion outer parameter. In this manner, a lip functions as a stable base to seat the prosthetic interface against a surface of the bone in which the bone anchor is implanted.

In an embodiment, the bone anchor has a tip end at the proximal end. The tip end may be rounded to reduce stress on the bone upon insertion. In this aspect, the bone anchor is a stem, having a proximal portion that is furthest inserted into bone, and an upper or distal portion toward the prosthetic interface. The distal portion of the bone anchor comprises a highly porous material, such as a coating of highly porous material. This coating may extend partway down the stem, or may extend substantially to the tip end. For mechanical integrity, the proximal portion of the bone anchor may be a solid stem without the porous material. To avoid or minimize unwanted rotation between the bone anchor and the bone in which the bone anchor is implanted, the solid stem may further comprise longitudinal splines. Alternatively, the stem is smooth and is cemented in place, thereby avoiding or minimizing unwanted rotational movement.

In an aspect, the solid stem is configured for press fitting, cementing, or both, into an intramedullary canal of the bone.

In an embodiment, a portion of the solid stem receives the through-hole, and the through-hole of the solid stem is threaded for receiving the fastener that connects the prosthetic interface with the bone anchor. This is one manner in which a reliable but reversible connection is established between the two pieces of the transcutaneous implant. Other connection means are provided, such as a friction-fit or tight-fit between male and female elements, or both fastener and friction-fit. The male element may be on either the prosthetic interface or the bone anchor, with the corresponding receiving passage on either the bone anchor or prosthetic interface, respectively. Alternatively, a partial threaded extractor bolt may be inserted into the longitudinal through-hole to aid in distraction of the elements of the design should that become necessary to facilitate removal of the bone anchor.

Alternatively, the invention relates to a method for implanting or a method of making or a method of using any of the transcutaneous devices provided herein.

In an embodiment, provided herein is a method for implanting a transcutaneous device for connecting an external prosthetic device to a bone by inserting a bone anchor into an intramedullary canal of the bone and providing a prosthetic interface. A fastener is passed through a through-hole of the prosthetic interface and a through-hole of the bone anchor and fastened to the bone anchor. In this manner, the prosthetic interface is connected to the bone anchor and the prosthetic interface is readied for receipt of an external prosthetic device. In an aspect, the method further comprises connecting the external prosthetic device to a distal portion of the prosthetic interface. Alternatively, the two device portions are tight-fitted to each other, such as be press-fitting the prosthetic interface to the bone anchor to reliably engage a male member in a corresponding receiving passage.

In an aspect, the step of inserting the bone anchor is by press-fitting, cementing, or both. In an aspect, the bone is within a residual limb, and the method further comprises opening the end of the residual limb; and reaming or broaching a bone canal of the bone. In an aspect, the method further comprises the step of closing soft tissues around the prosthetic interface by connecting soft tissues to a suture ring of the prosthetic connector.

In an aspect, the prosthetic interface is positioned outside the bone and skin overlaying the bone is attached to the prosthetic interface, including at a suture ring.

In an embodiment, the fastener is configured to be removed to facilitate extraction of the prosthetic interface or the prosthetic interface and the bone anchor. One example of a removable connector is a bolt that is threaded for engaging a threaded receptacle of the bone anchor through-hole. Rotational motion of the fastener provides means for engaging and disengaging the prosthetic interface and bone anchor.

Any of the methods and devices provided herein relate to a bone from a human or a non-human animal, such as an amputee where an external prosthetic serves to replace a limb. In an aspect, the limb is part of the leg, such as a bone that is a femur, or other bone for another limb, for example, tibia, metacarpal, humerus, forearm bone, phalanx, phalanges.

To further maximize tissue ingrowth, vascularization and tissue differentiation, the method optionally further comprises impregnating a highly porous coating portion of the bone anchor and the prosthetic interface that contacts biological tissue when implanted with antibiotics, anti-infectious chemicals, and/or morphogenic proteins (e.g., BMP, growth factors, cytokines to induce formation of a desired phenotype).

Another embodiment of the invention relates to a method of making a transcutaneous implant for connecting an external prosthetic device to bone, including any of the devices provided herein. In an aspect, the method comprises the steps of forming a through-hole in a bone anchor and a threaded portion of the through-hole for fastening a bolt thereto. A through-hole is formed in a prosthetic interface, wherein the prosthetic interface through-hole substantially matches the bone anchor through-hole through which the bolt fastened to the bone anchor passes, so that the bolt when present connects the prosthetic interface to the bone anchor. "Substantially matches" refers to the dimensions and position of the through-holes in each of the two pieces are functionally equivalent so that movement between the two pieces is avoided by a fastener that passes and connects the through-holes.

Any of the devices and methods provided herein optionally relate to a failsafe that is positioned between a prosthetic and the implant, thereby ensuring dangerous loads are not transmitted to the bone-implanted portion of the implant or to the bone of the amputee. Accordingly, any of the implantable transcutaneous devices provided herein may be described as a four piece system, comprising a stem, an abutment, a prosthetic interface (also referred herein as a prosthetic interface plug), and a failsafe break-away mechanism.

Also provided herein is a method of extracting any of the transcutaneous implants from a patient by removing the connector from the prosthetic interface, and distracting the prosthetic interface by rotation of a distraction bolt to impart a force against the bone anchor that acts to force the prosthetic interface away from the bone anchor and facilitate extraction of at least a portion of the implant. In an aspect, the distraction bolt corresponds to fastener and has a partially unthreaded portion to provide an extraction force exerted against the prosthetic interface. Alternatively, the fastener is different than the distraction bolt, and the fastener is removed and a distraction bolt inserted into the through-hole to generate the extraction force on the prosthetic interface.

DESCRIPTION OF THE DRAWINGS

FIG. 28: Animal 802, site 1. H&E stain at high power (100×). High magnification photo of the epidermal/dermal junction with porous tantalum implant post. Note the neutrophils (N) which are positioned superficial to the epidermis (E) showing a 'barrier' effect against inflammation of the soft tissues along the post of the implant.

FIG. 29: Animal 802, site 4. H&E stain at low power. Some of the porous tantalum implants experience epidermal down-growth such that the epidermis (E) contacts the base directly rather than the post. Most of the pores of the base portion of the implant are filled with vascularized connective tissue. Fibrous connective tissue (FCT) is present in the dermis adjacent to the implant on 3 sides.

DETAILED DESCRIPTION OF THE INVENTION

Figure 1:
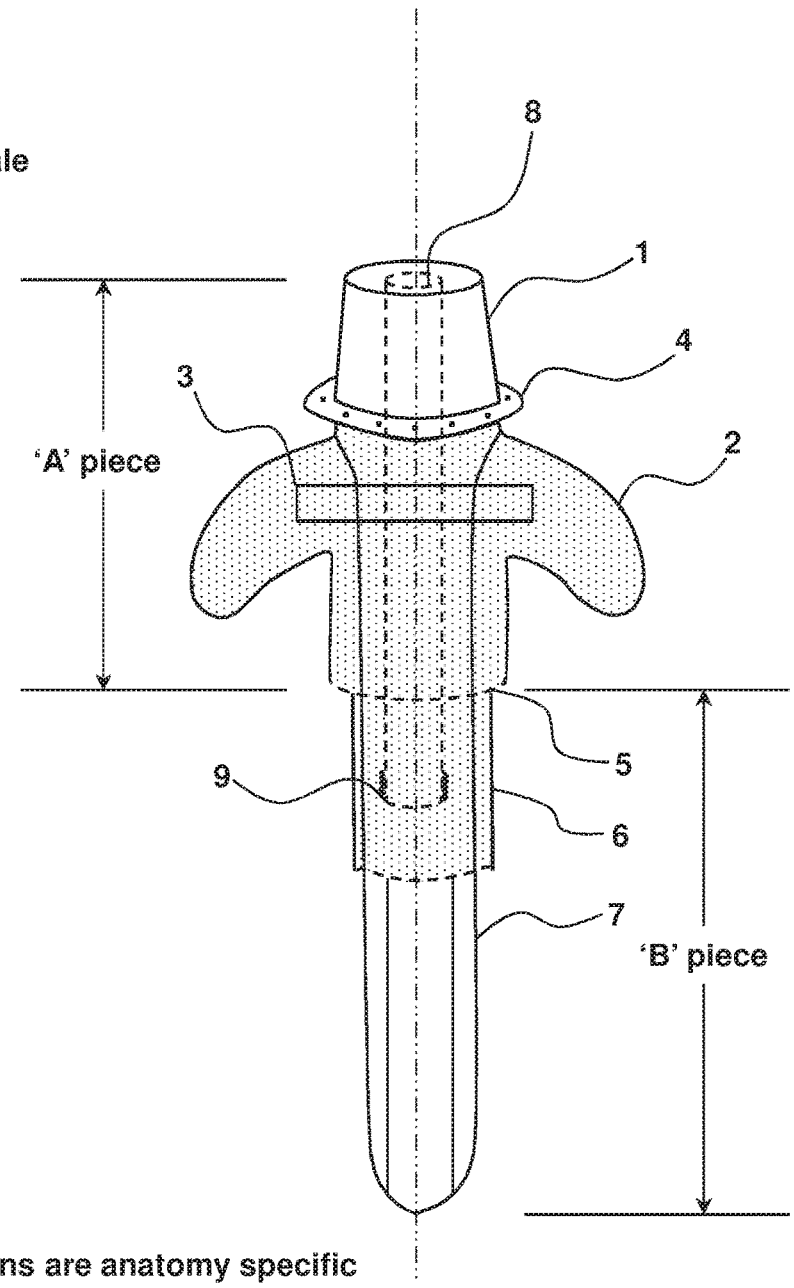
FIG. 1 is a schematic illustration of one embodiment of a two-piece transcutaneous implant device.

"External prosthetic device" refers to a device that replaces a missing body part, such as a device attached to the body that remains entirely external relative to the body. One example is a lower extremity prosthetic used to replace a lower leg that may have been amputated. The implant and prosthetic in combination may be transcutaneous in that one portion is within the body and another portion outside the body.

"Through-hole" refers to a passage in which a structure may be positioned, such as a fastener, to reliably connect two physically distinct components. In this example, the two physically distinct components are a bone anchor and prosthetic interface of the transcutaneous device each having a through-hole in which a single fastener may be positioned to fasten the components to each other or distract the two components, depending on the situation.

"Reversibly connected" refers to the ability to remove two components that are connected without substantially damaging the components or the functionality of the components. In an aspect, a reversible connection provides reliable connection, but is configured to be removed upon application of a force, such as a fastener that may be fastened and unfastened, as desired, such as by clockwise and counter-clockwise rotation of the fastener. A fastener that is used to distract the components may be referred to as an extraction bolt or distraction bolt.

"Distal" refers to a region or portion that is away from the trunk of the animal or person in which the device is implanted. "Proximal" refers to the region or portion that is toward or closer to the trunk of the animal or person in which the device is implanted.

"Highly porous material" refers to a surface in which the porosity facilitates tissue ingrowth of biological tissues. The level of porosity or parameter related to porosity (size, number, distribution, density) is selected to maximize tissue ingrowth, such as soft tissue or hard tissue ingrowth. In an aspect, the highly porous material has a porosity selected from a range that is between about 40% and 85%, or about 80%. Generally, higher porosity may be used for materials that coat a solid substrate, including a metallic substrate, as the solid substrate can provide mechanical stability. Generally, these materials comprise inter-connected pores with open-cell foam configuration.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. Thus, the scope of the invention should be determined by the appended claims and their equivalents, rather than by the examples given.

The implants provided herein provide a number of functional benefits, including avoiding skin breakdown that can occur for those prosthetics having a soft-tissue interface with the body. Instead, the implants provided herein are constructed to transmit forces directly between bone and prosthetic. This provides extremely efficient energy transfer, increased proprioceptive ability, improved tactile feedback and good fit independent of fluctuations in weight, muscular tone, edema, perspiration, level of activity, and body habitus.

There are certain other relevant attributes of the system that provide functional benefits and attendant improved implant outcome, including when compared to other devices, including WO2013/048589. Examples of attributes of the implant provided herein include the stem having a male end morse taper as well as the ability to reliably incorporate other connectors of other shapes, as desired, such as a pyramidal-shaped connector. Furthermore, the stem does not have a porous surface that abuts the end of the bone. Instead, the face that abuts the bone is part of the abutment component (see, e.g., 550 of FIG. 5), thereby making stem extraction, if necessary, easier. The through hole in the abutment is used to either screw down the abutment to the stem, or can be used alternatively to separate the stem and abutment (e.g., for a partially threaded bolt), if necessary. In addition, the surface of the bone anchor portion is uniform in that there are not recesses (in contrast to WO2013/048589 at element 32). A suture ring 540 positioned near the apex provides the ability to reliably intimately contact soft tissue (e.g., skin). Provided with any of the implants of the instant invention is an intercalary element or failsafe that connects to the prosthetic interface and controllably breaks away at forces less than the failure forces of the implanted components. In a functionally similar manner to a ski binding to release boot from ski to minimize injury, the failsafe ensures and implant failure occurs outside the body, including a "controlled" implant failure so that the implant may be reconnected and/or reset as desired after failure.

The shaped tissue ingrowth surface (e.g., bulbous, umbrella-shaped, skirt-shaped or mushroom shaped) allows more surface area for ingrowth of soft tissues and decreases the likelihood that infection will circumvent the implant and infect the underlying or adjacent bone. In combination with the shaped tissue ingrowth surface, a structural enhancer element such as metallic circumferential 'rib' or ring is included within the porous umbrella portion of the abutment to mechanically support this region.

A threaded 'prosthetic interface plug' can unscrew, revealing a locking bolt below. This locking bolt can be removed and replaced by a 'distraction bolt' which is partially threaded to allow dissociation of the abutment and stem if necessary for ease of extraction.

In contrast to WO2013/048589 (e.g., FIGS. 7A-C of WO2013/048589 showing tapered implant), the implant provided herein does not require a tapered portion of the stem.

Example 1: Two-Piece Transcutaneous Device

Figure 2:
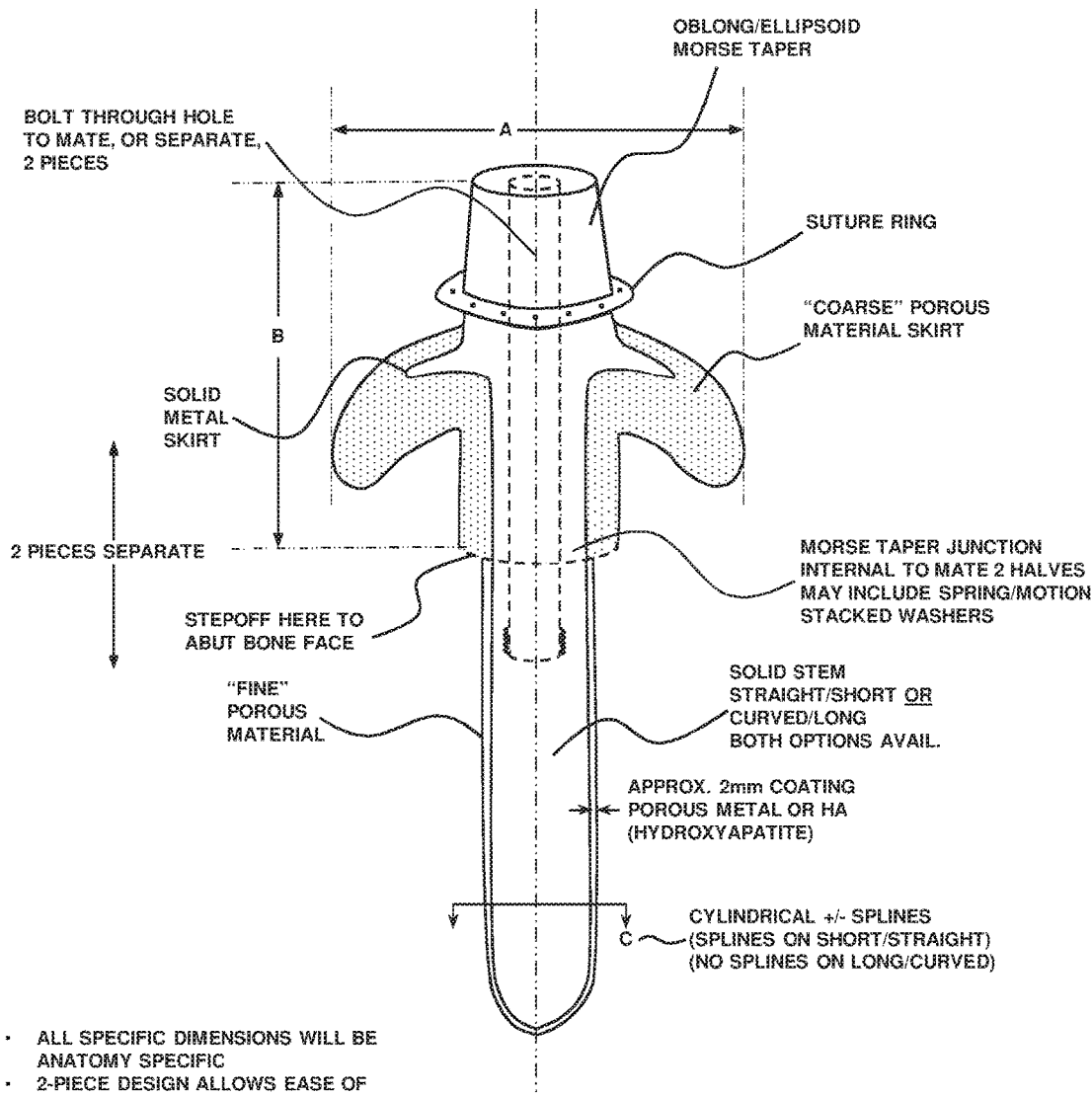
FIG. 2 is a schematic illustration of another embodiment of a two-piece transcutaneous implant device.

FIGS. 1-2 illustrate a two-piece transcutaneous device designed to provide a bone anchor in the bone of a residual limb or digit in an animal (human or non-human) for direct skeletal attachment of an external prosthetic device. The device uses highly porous coating along the majority of its length to act as a matrix for biologic ingrowth of various tissues.

The biologic ingrowth at the bone interface (in and around 5 of FIG. 1) is bony and facilitates rigid, stable, and durable fixation of the implant to the bone. The biologic ingrowth in the soft tissues in and around 2 (skin, subcutaneous tissue, muscle) provides an effective barrier against infection at the bone/implant interface due to its vascularity—making available white blood cells and antibiotic delivery via blood vessels if necessary to ward off advancing bacteria.

The device is illustrated as two separate pieces, 'A' Piece ("prosthetic interface") and 'B' Piece ("bone anchor"). These two pieces are mated at the elbow labeled 5 in the diagram and is referred herein as a "stable base". They are held together with a fastener (not shown) that can be a threaded bolt that slips down the center of the implant through the through-holes of A and B pieces as indicated by the dashed lines. One benefit of the two piece design is ease of extraction should the implant need to be removed. The extraction process involves removing the locking bolt, inserting a partially threaded distraction bolt, disengaging piece 'A', and using a cylindrical trephine to remove piece 'B' from the bone.

The cross-hatched regions of the implant represent a highly porous material, such as a coating on a solid substrate. In FIG. 1, the cross-hatched is on a distal portion of the bone anchor and a proximal portion of the prosthetic interface. The pore sizes/diameter may be varied from region to region on the implant to facilitate ingrowth by the target tissues (i.e. smaller pore sizes for bone ingrowth, and larger pore sizes for soft tissue ingrowth). The highly porous coating may be impregnated with antibiotics, anti-infectious agents/chemicals, or morphogenic proteins to help reduce risk of deep infection and help facilitate/steer the differentiation of tissues that permeate the material. In an aspect, the coating is about 1 mm to about 5 mm thick and covers a solid substrate, wherein ingrowth does not substantially occur into the solid substrate. In this manner, only an outermost layer of the implant has tissue ingrowth.

Referring to FIG. 1, 1 refers to a distal end of the prosthetic interface for connecting to an external prosthetic device (not shown), and can be a male end Morse taper. The end can be shaped cylindrically or oblong with the purpose of mating the osseous integration implant provided herein with an external prosthetic device. Optionally, the external prosthetic device is designed such that its failure loads are less than that of the osseous integration device itself—allowing for mechanical failure of the prosthetic interface before the osseous integration implant itself fails. A male-end Morse taper system uses a mating interface so that the prosthetic end such as the female end of the Morse taper is the weak link in the mechanical system. This avoids implant failure and minimizes need for revision surgery with extraction/insertion of the implant.

Element 2 illustrates a shaped tissue ingrowth surface. The rounded 'shoulder' of porous materials ("rounded radial edge") facilitates and maximizes soft tissue ingrowth and vascularization. This rounding is to create an extensive network of vascularized tissue through which bacteria must circumnavigate to get to the bone/implant interface. By rounding this and creating an 'umbrella' shape, this creates more of a vascular barrier against infection and more surface area for the skin to integrate and stabilize on the implant, thereby improving implant success and long-term reliability. The apex region corresponds to the region of the surface furthest from the proximal end. The outer facing surface is distal-facing and is referred to as convex. The inner facing surface faces in a proximal direction and is referred to as concave-shaped. This configuration can maximize surface area available for soft-tissue ingrowth without unduly sacrificing mechanical stability. Sharp-edged surfaces, in contrast, have corners that are not as accessible for ingrowth and may create stress risers.

In another embodiment, the shaped tissue ingrowth surface has a surface shape that is bulbous. Bulbous refers to a generally bulb shaped surface that does not have any sharp corners or edges, but instead has a varying curvature depending on the surface position, such as for a conventionally shaped bulb.

A structural enhancer such as a solid metal ring 3 (indicated as "solid metal skirt" in FIG. 2; also referred herein as a "structural enhancer element") helps to mechanically stabilize the rounded 'shoulder' of porous materials.

A suture ring 4 is placed at the base of the Morse taper and at the apex of the rounded 'shoulder' of porous material to provide an anchoring point for the skin upon implantation of the device. This anchor point helps stabilize the skin edge upon implantation and allows the skin to permeate the porous metals and provide barrier against deep infection.

A step-off region 5 of porous material is meant for the bone face. The implant above this line (piece 'A'—prosthetic interface) is all external to the bone, while piece 'B' (bone anchor) is configured to be intramedullary within the bone. This provides a stable base for seating of the implant and also provides a bony ingrowth medium to prevent deep infection.

Bone anchor distal portion or region 6 having a highly porous material coating is designed to be intra-medullary and facilitate bone ingrowth for stabilization of the implant. Note that the highly porous material may or may not extend to the tip of the stem. If the patient is deemed at risk for stress shielding phenomenon, the ingrowth coating here can be shortened such that the lower stem (e.g., a proximal portion of the bone anchor) is not coated with highly porous material.

Solid stem 7 of the bone anchor can have longitudinal splines to promote rotational stability upon initial implantation or can be smooth, so long as the press-fit and/or cementing results in a sufficiently strong fit to avoid unwanted rotation during use. The cross-sectional shape, dimensions and length of the stem is anatomy specific at this location. The tip end of the proximal-most end of the stem can be bullet-shaped or rounded to reduce stress on the bone upon insertion. This is configured to be press fit or cemented into the host bone intramedullary canal.

Through-hole 8 receives a fastener, such as a threaded bolt that mates piece 'A' to piece 'B'. In order to separate the pieces from one another, the bolt is removed and an extraction device that separates the two is employed. Again, one purpose of this design feature is to allow for ease of extraction of the implant if necessary. Threaded receptacle 9 (built into through-hole of piece 'B') mates the two pieces with fastener such as the drop-through threaded bolt described above.

Example 2: Prosthesis for Transfemoral Amputees

Figure 3:
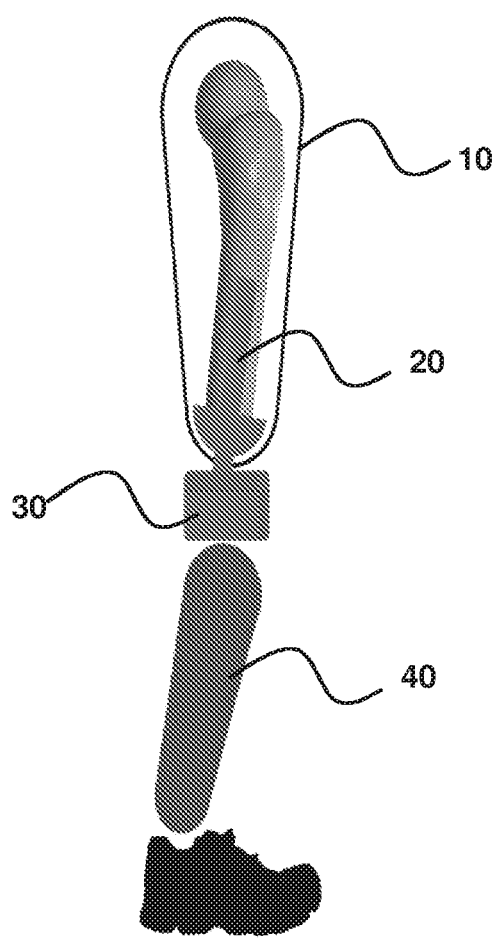
FIG. 3 is a diagram illustrating various subsystems for an embodiment relevant for an implanted transcutaneous device, including the patient (e.g., biological tissue such as a residual limb comprising bone and soft tissue), the implant, the prosthesis, and optionally a failsafe for ensuring damaging forces are not transmitted to the implant that could damage the biological tissue (e.g., fracture bone).

An example of a prosthesis for use by transfemoral amputees is illustrated in FIG. 3. The overall system can be characterized into different subsystems: the patient 10 (residual limb), implant 20, prosthesis 40 and, optionally, a failsafe 30 that operably connects the prosthesis 40 to the implant 20, including any of the two-piece transcutaneous devices disclosed herein. The failsafe functions as an interface between the prosthesis and the implant and, therefore, the patient; in particular the bone that surrounds the bone-implanted portion of the implant. As further discussed below, system load is empirically measured by force or pressure transducers, computationally determined such as by finite element analysis, and/or obtained from the literature. In this manner, the loads exerted on bone by the implant in various settings are determined. With such loads known, as well as the strength of patient's tissue such as bone strength and bone failure of fracture load, the system is designed to ensure that loads that would otherwise be potentially damaging are not transmitted to the patient. This may be achieved via the failsafe 30 which disconnects the implant from the prosthesis at a defined load, force or pressure.

Several studies contribute in assessing loading conditions for amputees. In most circumstances, loads are measured directly at the abutment (distal end of the implant) by means of a load transducer. Some of the examined movements include walking, ascending and descending stairs, ascending and descending a ramp, walking in a circle, falling, and running [8] [9]. The literature-obtained measures may be used to: 1) gain knowledge regarding the range of loading conditions typical of common activities, 2) implement loading into preliminary static and future dynamic FE models to determine implant design, and 3) develop criteria for the failsafe 30. One study by Lee et al is examined to set baseline loading profiles during walking. [10] While walking data are valuable to understand the required loading and can provide useful model information, other movements are assessed to better characterize risk. For preliminary static analysis, a peak loading condition from force and moment profiles is selected. Examples of loading values obtained from the literature are provided in Tables 1 and 2, with the forces and moments defined as: $F_{AP}$: Force in the anterior-posterior direction (anterior positive); $F_{ML}$: Force in the medial-lateral direction (medial positive); $F_{IS}$: Force in the inferior-superior direction (superior/compressive positive); $M_{AP}$: Moment in the anterior-posterior axis (lateral rotation positive); $M_{ML}$: Moment in the medial-lateral axis (anterior rotation positive); $M_{IS}$: Moment in the inferior-superior axis (external rotation positive). The positive and negative signs reflect the specific direction along the relevant axis.

Since the loads corresponding to the subject are dependent on their body weight, the normalized values are of primary interest. For finite element analysis (FEA) of the average femur model and for quantifying daily activities for the failsafe mechanism, the normalized value is multiplied by body weight and divided by one-hundred in order to accurately represent the average male. Further, loads are assessed at the distal end of the implant of a transfemoral amputee during a forward fall. [9] That study involved a subject who has an implant, and while the fall did not cause harm to the subject, the collected loading data is useful for determining harmful loads. Table 3 below presents the peak forces and moments that occurred at the abutment during this fall.

From these peak loading values, the moment in the inferior-superior direction ($M_{IS+}$ and $M_{IS-}$) are largely of interest because this corresponds to the axial torque applied to the implant and femur.

Figure 4:
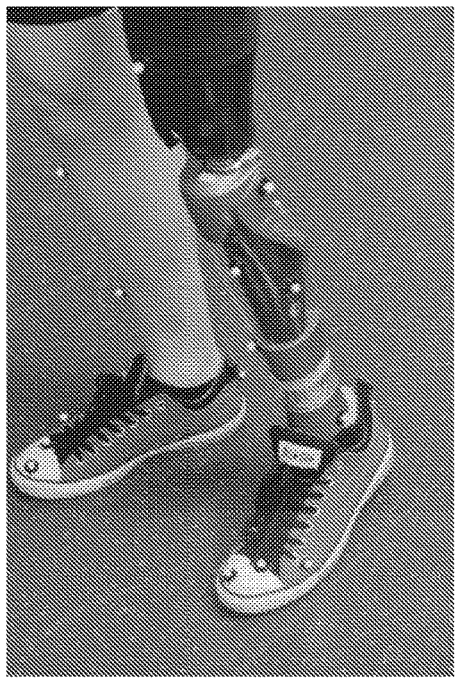
FIG. 4 illustrates an experimental process for ground reaction force capture (A) and corresponding development of a skeletal model to determine joint loads under loads associated with various ground reaction forces (B).
Figure 4:
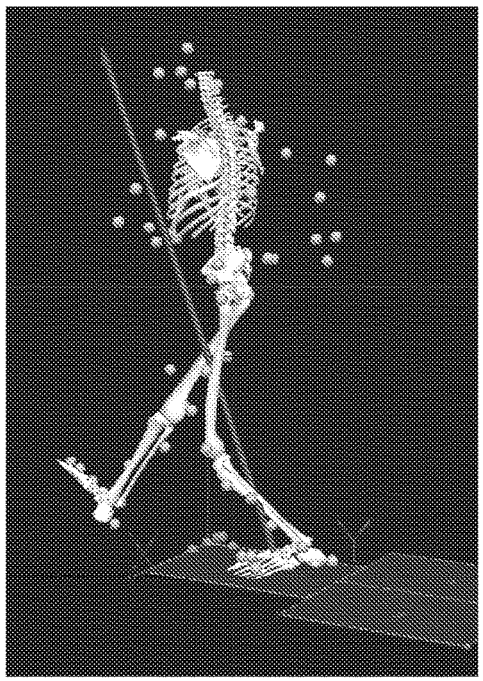

The literature-based loading information is further supplemented, verified and extended by empirical measurements in a Human Dynamics Laboratory (HDL). Examples of activity and corresponding measured loads include sit-to-stand, normal gait, pivots, stairs, getting up from the ground, jog, jump, trip, ankle roll and turn. The measurement may be performed by an amputee or a non-amputee. This load determination is illustrated in FIG. 4, with the left panel illustrating motion and capture, and the right panel a corresponding skeletal model to resolve joint loads. The results are compared to published literature with maximal knee loads in six degrees-of-freedom calculated via inverse dynamics. The loads of highest risk are confirmed to be axial torque and bending.

Normalized forces and moments are compared between literature and HDL collections and ranges obtained. This quantifies the upper limit associated with daily living (DL). The obtained data is summarized in Table 4. The data may be further verified and refined so as to ensure typical and upper-limit load ranges are accurate for a number of different situations.

Figure 5:
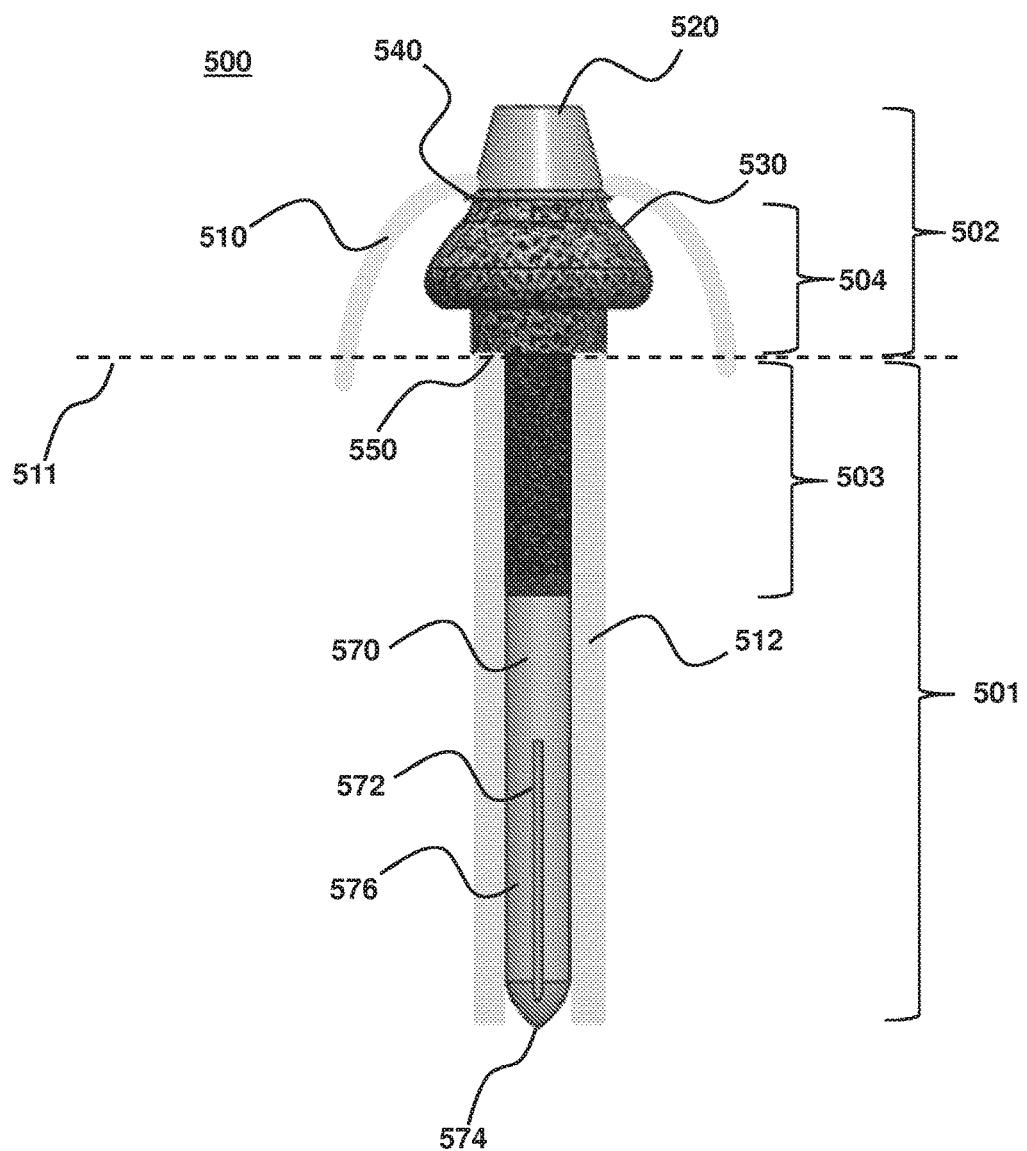
FIG. 5 is a schematic of a two-piece transcutaneous implant to connect a prosthetic to a patient, such as a lower limb prosthetic to a femur bone. The two pieces include a soft-tissue and bone integration component referred herein as prosthetic interface and bone anchor, respectively.

One example of an implant of the present invention is provided in FIG. 5. The implant or transcutaneous device 500 is generally referred to as "transcutaneous" because when implanted a portion (e.g., bone anchor 501) of the device 500 is beneath skin 510 and another portion (e.g., prosthetic interface 502) extends beyond the skin surface 510. The dashed line 511 indicates the bone/soft-tissue interface, with the region above the dashed line corresponding to implant that facilitates soft tissue integration with the implant, and the region below the line corresponding to implant that facilitates bone integration with the implant. Accordingly, the device may be described as having a bone-tissue ingrowth portion 503 and a soft-tissue ingrowth portion 504.

The prosthetic interface 502 may have a distal end that is a male end of a Morse taper 520 to connect the implant directly to an external prosthesis or, alternatively, to a failsafe (not shown). The device may have a shaped tissue ingrowth surface 530, such as an "umbrella" shaped surface made of a porous material or materials to facilitate soft tissue in-growth and vascularization. A structural enhancer element (not shown) may be positioned within the shaped tissue ingrowth surface of the prosthetic interface to provide mechanical support to the rounded shoulder of the porous material. In an aspect, the structural enhancer element is a solid ring, such as a solid metal ring, that is positioned around the central shaft (not shown) of the device. A suture ring 540 is an anchoring point for the skin 510 to set implant position relative to the skin and to promote skin ingrowth into the porous materials to generate a biologically tight skin-implant interface that assists in preventing or avoiding infection. In the embodiment of FIG. 5, the suture ring 540 is positioned at an apex region of the tissue ingrowth surface 530.

An elbow or step-off region 550 of porous material may further assist with implant positioning. The step region 550 also delineates the bone tissue ingrowth portion 503 from the soft tissue ingrowth portion 504, as indicated by dashed line 511 where the portion of the implant below line 511 is within bone 512 and the implanted portion of the device above the line 511 is within soft tissue with optionally a portion external to the body. Bone tissue ingrowth portion 503, similar to soft tissue ingrowth potion 504, comprises a highly porous material. In an embodiment, the highly porous materials correspond to each other. In an embodiment, the highly porous material of the soft tissue ingrowth portion is different than the highly porous material of the bone tissue ingrowth portion, such as having porosity, pore sizes, growth factors and the like tailored to facilitate ingrowth of the desired cell type (e.g., soft versus hard tissue). Optionally, the mechanical properties of the implant portions are selected to match mechanical properties of the surrounding tissue, such as a modulus including Young's modulus, thereby minimizing compliance mismatch between implant and surrounding biological tissue.

Bone tissue ingrowth portion 503 may extend a defined length of the solid stem 570, up to and including the entire length of the solid stem 570. FIG. 5 illustrates bone tissue ingrowth portion 503 that extends less than half the longitudinal length of the bone anchor region 501. Optionally, solid stem 570 has splines 572 running in a longitudinal direction along at least a portion of the solid stem 570. Splines 572 may help prevent unwanted rotational motion of the implant relative to surrounding bone. Optionally, the tip or a distal portion of the bone anchor 501 has a cross-sectional shape that is elliptical. Optionally, the tip 574, a portion, or all of the bone anchor has a cross-sectional shape that is substantially circular or is circular. Optionally, a distal-most portion of the bone anchor has an elliptical cross-section that transitions to a circular cross-section 576 in a direction that is toward the residual limb surface. An elliptical cross-section toward or at the tip of the implant may reduce stress when the implant is inserted into bone. Optionally, the tip 574 is tapered. The modular design outlined herein allows for extraction of the soft tissue ingrowth or prosthetic interface 502 without removing the bone-implanted portion, thereby avoiding or minimizing the need for a more invasive medical procedures.

Figure 6:
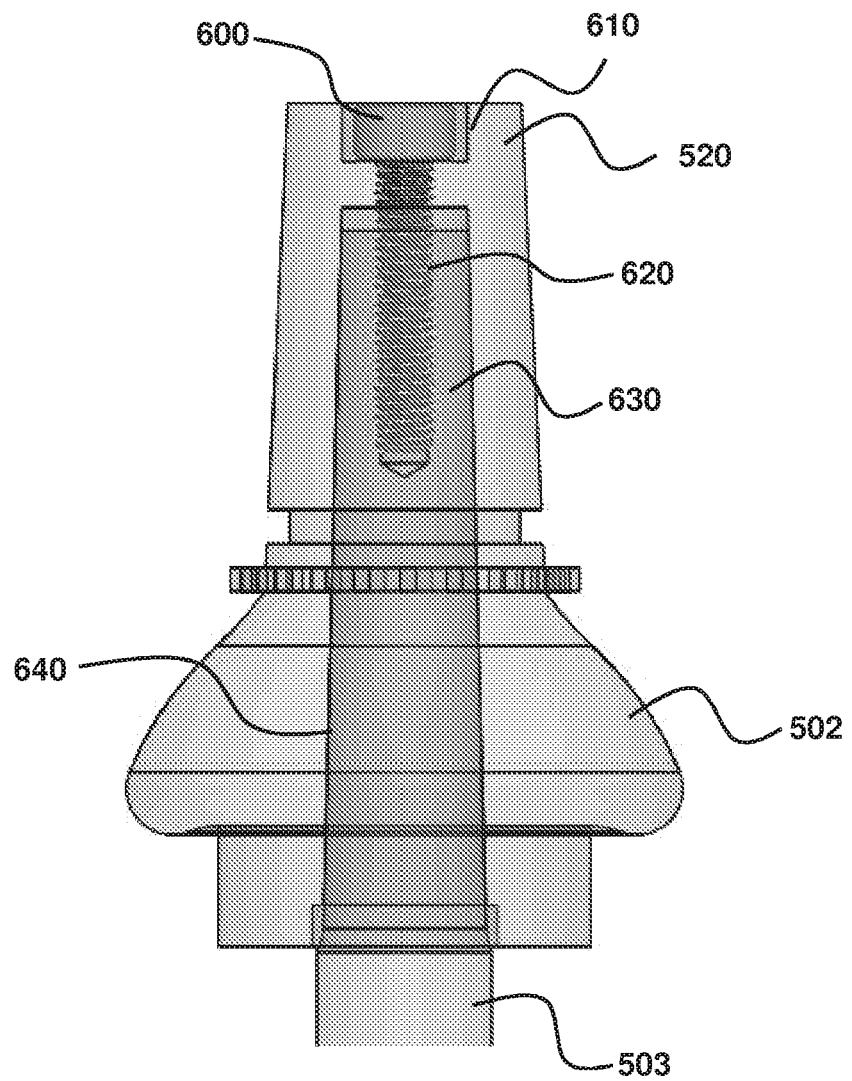
FIG. 6 is a transparent view of a taper within the prosthetic connection to receive a portion of the bone anchor.

FIG. 6 is an illustration focused on the connection features of the device. Any one or more connection means may be employed. For example, the taper connection 520 may contain a fastener such as a locking bolt or screw 600 that connects the bone anchor portion 503 to the prosthetic interface 502 (including, e.g., the soft tissue ingrowth portion). Furthermore, the prosthetic interface 502 may contain a through-hole 610 (e.g., threaded through-hole) for receiving the screw 600. Similarly, the bone anchor portion may contain a threaded receptacle or passage 620 for receiving screw or bolt 600. In addition or in alternative, the two pieces may mate via a tight-fit connection, such as a tapered connecting so that the two pieces press-fit with respect to each other. Referring to FIG. 6, male end 630 of bone anchor 503 may be received by a passage 640 contained within the interior of prosthetic interface 502. In an aspect, the connection may be via a tapered passage 640 and corresponding tapered male end 630. In an embodiment, the connection is by the combination of a fastener and press-fit.

Figure 7:
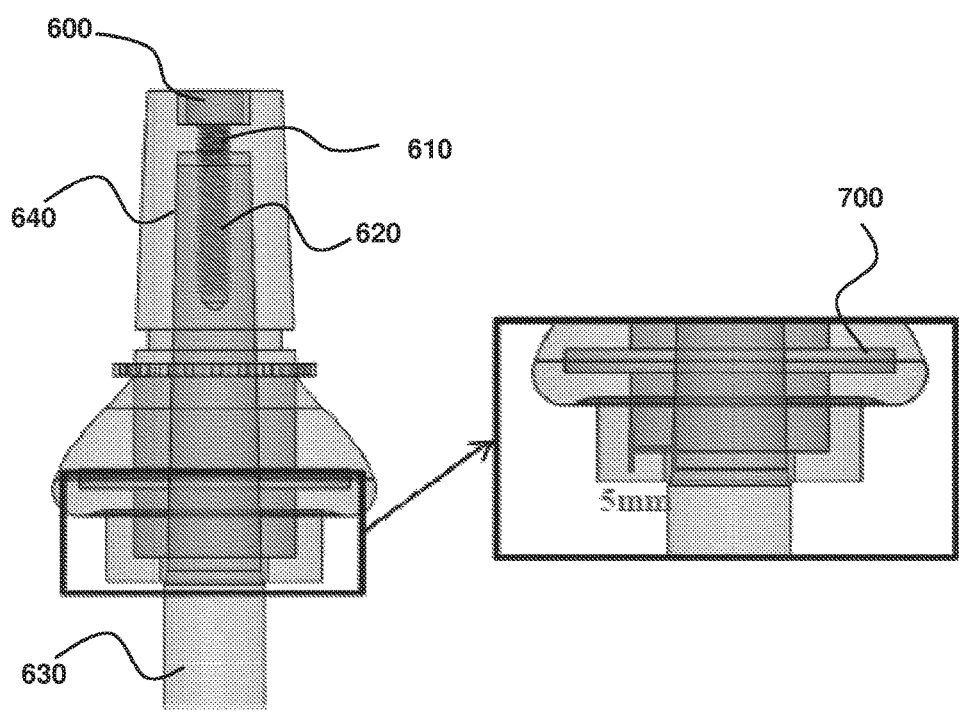
FIG. 7 is a transparent view of a taper within the prosthetic connection to receive a portion of the bone anchor. The image on the right is a blown-up view of the area indicated by the box in the image on the left.

FIG. 7 shows the male member 630 taper set within the Soft Tissue Integration component (transparent in this image), also referred herein as prosthetic interface 502 or soft tissue ingrowth portion. On the right is a blown-up view of the interface between the two components: the bone anchor and the prosthetic interface. The structural core of the Soft Tissue Integration component has a minimum thickness of 5 mm, with the central portion comprising a passage 640 for receiving the bone anchor male member. There is also a small clearance between the beginning of the taper and the Soft Tissue Integration component which allows the taper to further set under loading, thus strengthening the connection. A structural enhancer element 700, such as a solid ring, is shown within the prosthetic interface, and more particularly, within the shaped tissue ingrowth surface. Optionally, fastener 600 is used to further fasten two components of the device, such as male member 630 within a receiving passage 640.

Figure 8:
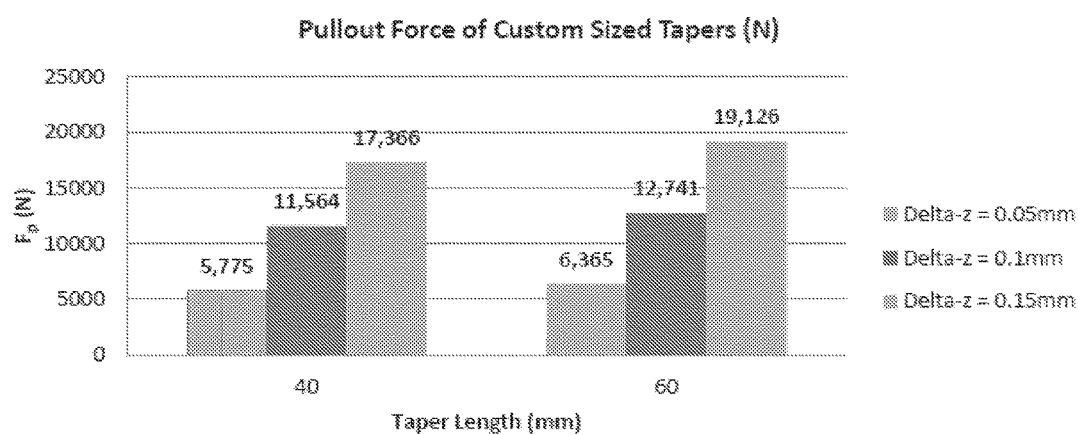
FIG. 8 is a plot of the pullout force determined for a taper having: large end diameter 14 mm; small end diameter 11 mm, and length 40 mm (taper angle of 1.49°) or 60 mm (taper angle of 2.15°) for indicated delta-z (corresponding to the distance the taper is pressed into the housing when set).
Figure 9:
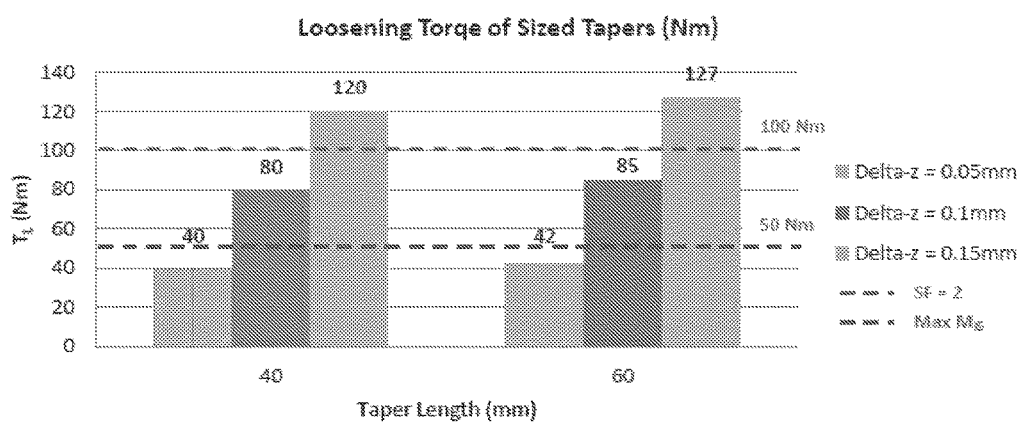
FIG. 9 is a plot of the loosening torque determined for a taper having: large end diameter 14 mm; small end diameter 11 mm, and length 40 mm (taper angle of 1.49°) or 60 mm (taper angle of 2.15°) for indicated delta-z (corresponding to the distance the taper is pressed into the housing when set).

The pullout and loosening torque for different tapers and distance the taper is pressed into the housing is summarized in FIGS. 8 and 9.

The pullout forces shown in FIG. 8 greatly exceeds all tensile loads the implant encounters discussed above. Loosening torques of the tapers are relatively close to what is expected to occur in normal day-to-day activity. The maximum torque is determined to be approximately 50 Nm (shown as the lower dashed line in FIG. 9). This value is calculated based on the average male weight. This torque corresponds to an inferior-superior moment recorded from the HDL data collection for a non-amputee. As shown in FIG. 8: Loosening torque calculated for the taper options indicates the maximum expected day-to-day torque is greater than the loosening torque for both tapers with a minimum Δz of 0.05 mm. The loosening torques for the larger values of Δz exceeds the maximum day-to-day torque value of 50 Nm. In order to design for a safety factor of two, the tapers may be assembled with a Δz of 0.15 mm or higher.

These results indicate that the tapered interference fit does not require an additional feature for rotational stability for a Δz of 0.15 mm or higher. Since there is some uncertainty as to whether a Δz of 0.15 mm can be reliably achieved during use, a locking bolt/screw mechanism may be included to serve as an additional stability feature. This locking bolt or screw may later be removed if a Δz of 0.15 mm is reliably and consistently achieved during the taper assembly.

Figure 10:
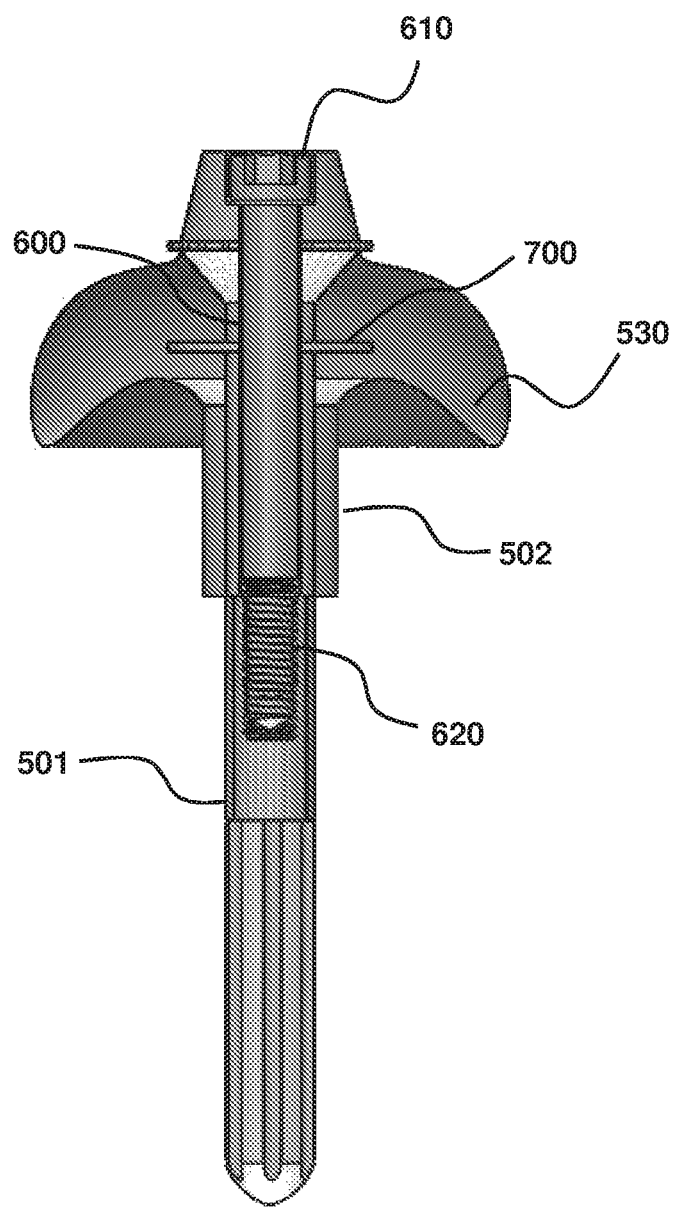
FIG. 10 is a section view of an implant with a fastener connection between the bone anchor and the prosthetic interface.
Figures 11, 12:
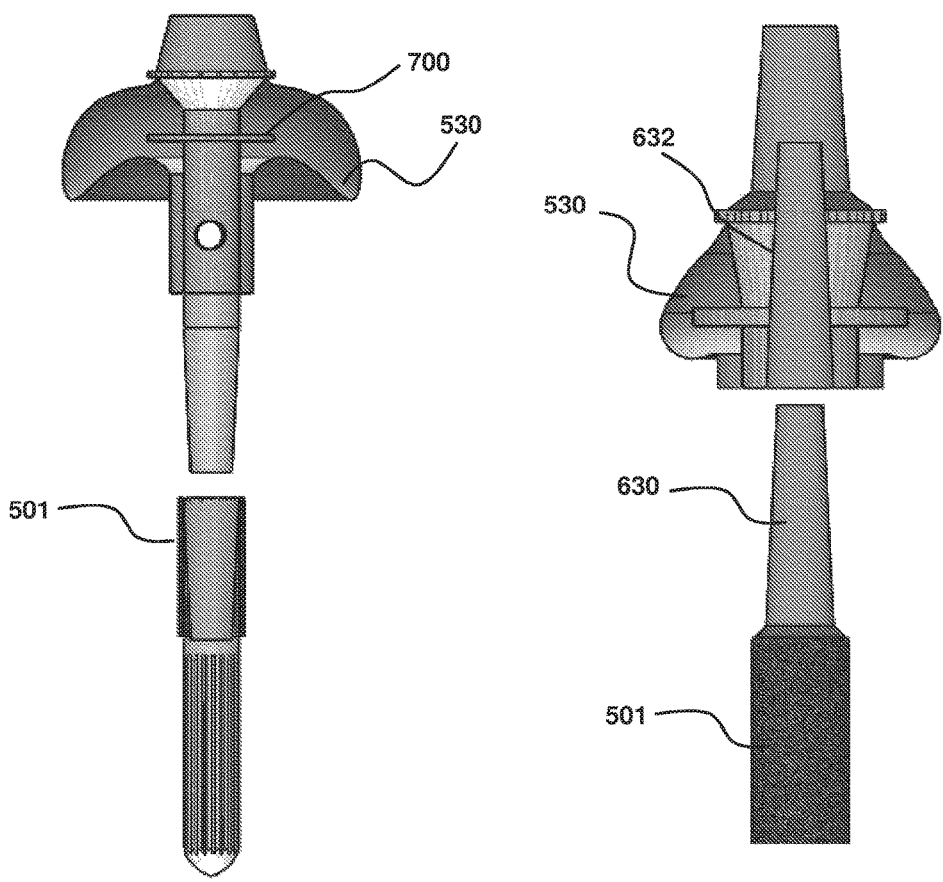
FIG. 11 is a section view of an implant with a tapered interference fit between the bone anchor and the prosthetic interface having male member.
FIG. 12 is an exploded sectional view of a tapered interference fit between the bone anchor having male member and the prosthetic interface.

Examples of mechanisms to connect the bone anchor and prosthetic interface are summarized in FIGS. 10-13. FIG. 10 shows a fastener (long bolt or screw) 600 connection through the longitudinal axis of the prosthetic interface 502 and bone anchor 501 (compare to the shorter fastener (bolt or screw) 600 of FIG. 6). Accordingly, in an aspect, the fastener extends through and past shaped tissue ingrowth surface 530 or terminates before the shaped tissue ingrowth surface 530 (compare, e.g., FIGS. 6 and 10). The prosthetic interface piece of the transcutaneous device may then be simply removed by removing the locking bolt 600.

In contrast to the fastener systems of FIG. 10, FIGS. 11-13 illustrate different systems that employ of tight-fit or press-fit between the two components of the implant, referred herein as a "tapered interference fit". The interference fit systems relies on frictional forces to hold the two components of the implant together. During prosthetic use, the loads transmitted to the implant further strengthens the interference fit. If no fastener is used, no through-hole is required which may further strengthen the implant, particularly the prosthetic interface 502 portion. Structural enhancer 700, such as a solid ring, assists with structural integrity and strength of the shaped tissue ingrowth surface 530.

Figure 13:
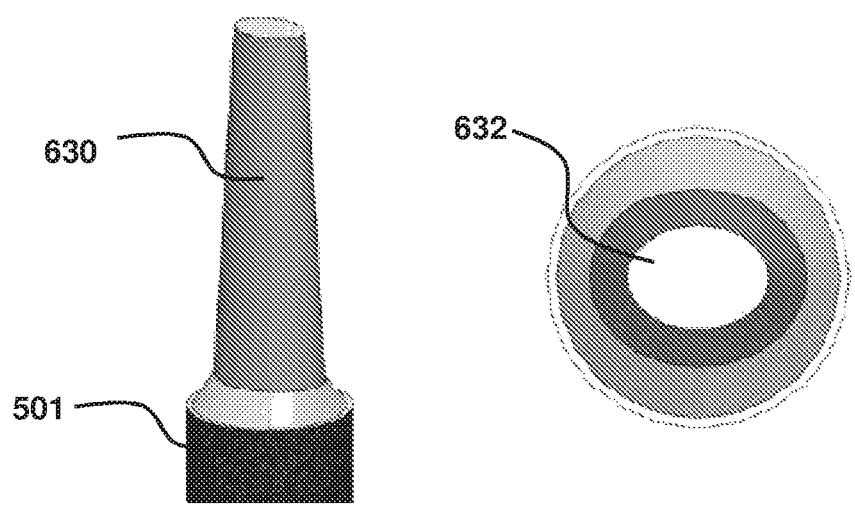
FIG. 13 shows the male end of an oblong taper having an oval shape.

To address concerns related to rotational stability, an oblong shaped taper of FIG. 13 may be used, where the male member 630 of the bone anchor has a non-circular cross-sectional shape matched to the counterpart receiving passage 632 in the prosthetic interface. One suitable cross-sectional shape is elliptical, wherein the cross-section is defined by a major radius and a minor radius. Alternative means are available. For example, use of set screws on different sides of the stem may control concerns associated with unwanted rotational motion.

Figure 14:
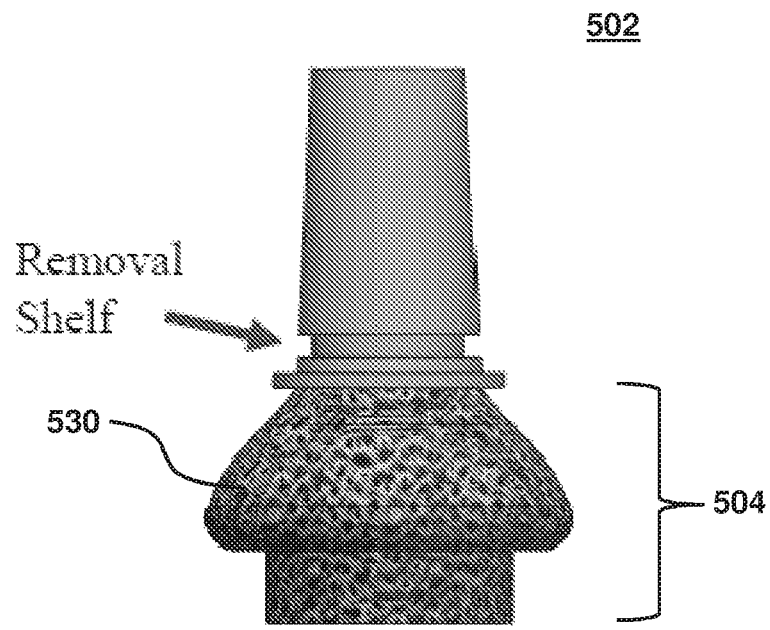
FIG. 14 illustrates one embodiment of an implant prosthetic interface.
Figure 15:
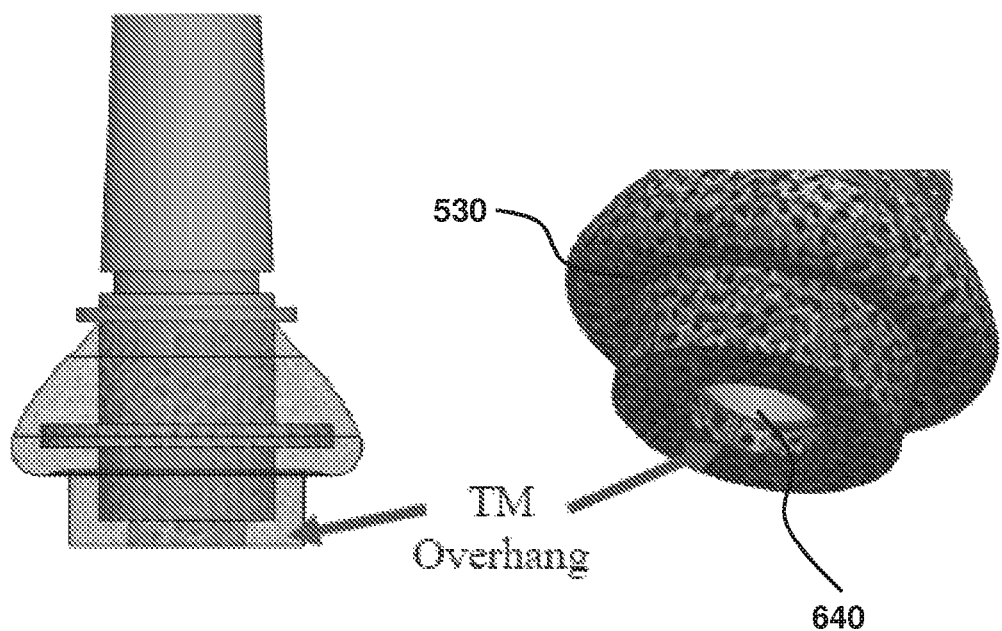
FIG. 15 illustrates a porous material that is trabecular metal (TM) having an overhang.

Soft tissue integration: The prosthetic interface 502, focused on the soft-tissue ingrowth portion 504 and shaped tissue ingrowth surface 530 is illustrated in FIG. 14. A removal shelf may be positioned in a more physically-accessible position at the top portion of the porous material. FIG. 15 shows the solid core of the prosthetic interface and a porous material (e.g., trabecular metal or "TM") on the proximal end of the piece along with receiving passage 640. The overhang allows the entire bone face to fit flush with the TM allowing for optimum bone in-growth at the soft-tissue/bone-tissue/implant interface.

Bone integration: The Bone Integration component (e.g., bone anchor 501) of the implant includes the stem that is inserted into the medullar canal of the femur. The shape of this stem is dependent on the size and shape of the femur in addition to the location at which the femur is cut during surgery. The stem may be tailored to a specific individual. The stems described herein correspond to an "average" femur model.

Three stems options are provided. These options include a straight and curved press-fit stem and a straight cemented stem. These stems are designed for use with different cut lengths within the femur model. The straight stems are designed for the femur model cut 240 mm and 180 mm proximal of the lateral epicondyle. The bent stem is designed for the femur model cut 120 mm and 180 mm proximal of the lateral epicondyle.

Figure 16:
FIG. 16 is a transcutaneous device for implantation having a length of 140 mm and 15 mm diameter.
Figure 16:
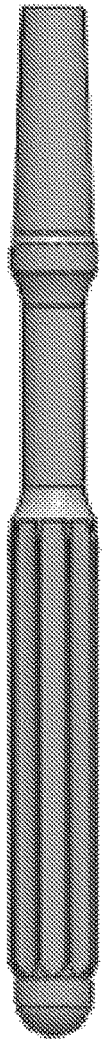
Figure 16:
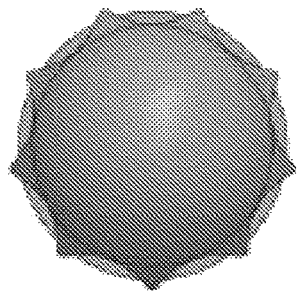

The straight stem is 140 mm in length and 15 mm in diameter. This stem is designed for the average femur model cut 240 mm and 180 mm proximal of the lateral epicondyle. FIG. 16 shows the 140 mm straight stem. The image on the left shows the entire press-fit stem with the TM. The image in the middle shows the rigid core of the implant without the TM. The image on the right shows the geometry of the sharp splines looking down the stem longitudinal axis. These splines are designed to provide an interference fit of roughly 0.5 mm with the bone.

Figure 17:
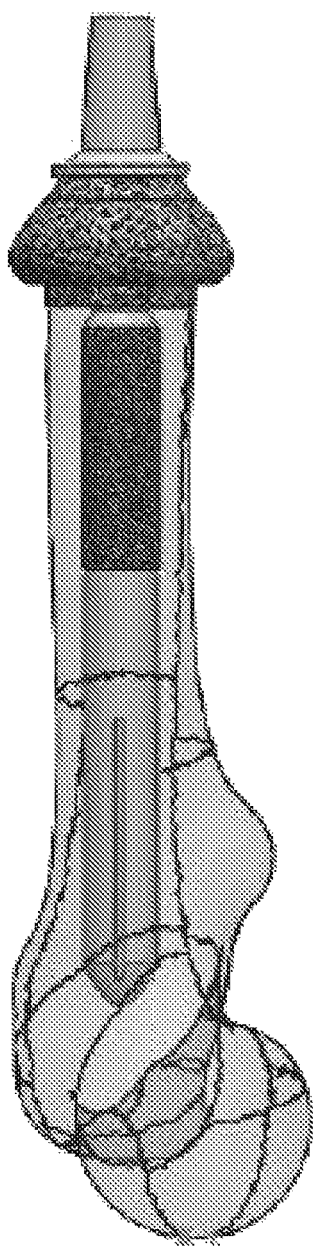
FIG. 17 is a straight stem implanted in femur cut 190 mm distal of femoral head.
Figure 18:
FIG. 18 illustrates straight (left panel) and curved (right panel) stems for implantation into bone tissue.

The diameter of this stem is selected to fit within the medullar canal of the femur model while providing a tight press fit into the endosteum. FIG. 17 shows the 140 mm length stem within the femur model cut 240 proximal to the lateral epicondyle. Other implant parameters that may be varied, depending on the amputation location and bone morphology, are illustrated in FIG. 18. For example, the bone implanted stem may be straight (FIG. 18 left panel) or may be bent or curved (FIG. 18 right panel). The splines may have a sharp surface for straight stems or may have a smooth surface to facilitate insertion of the bent stem into bone during a surgical procedure.

Figure 19:
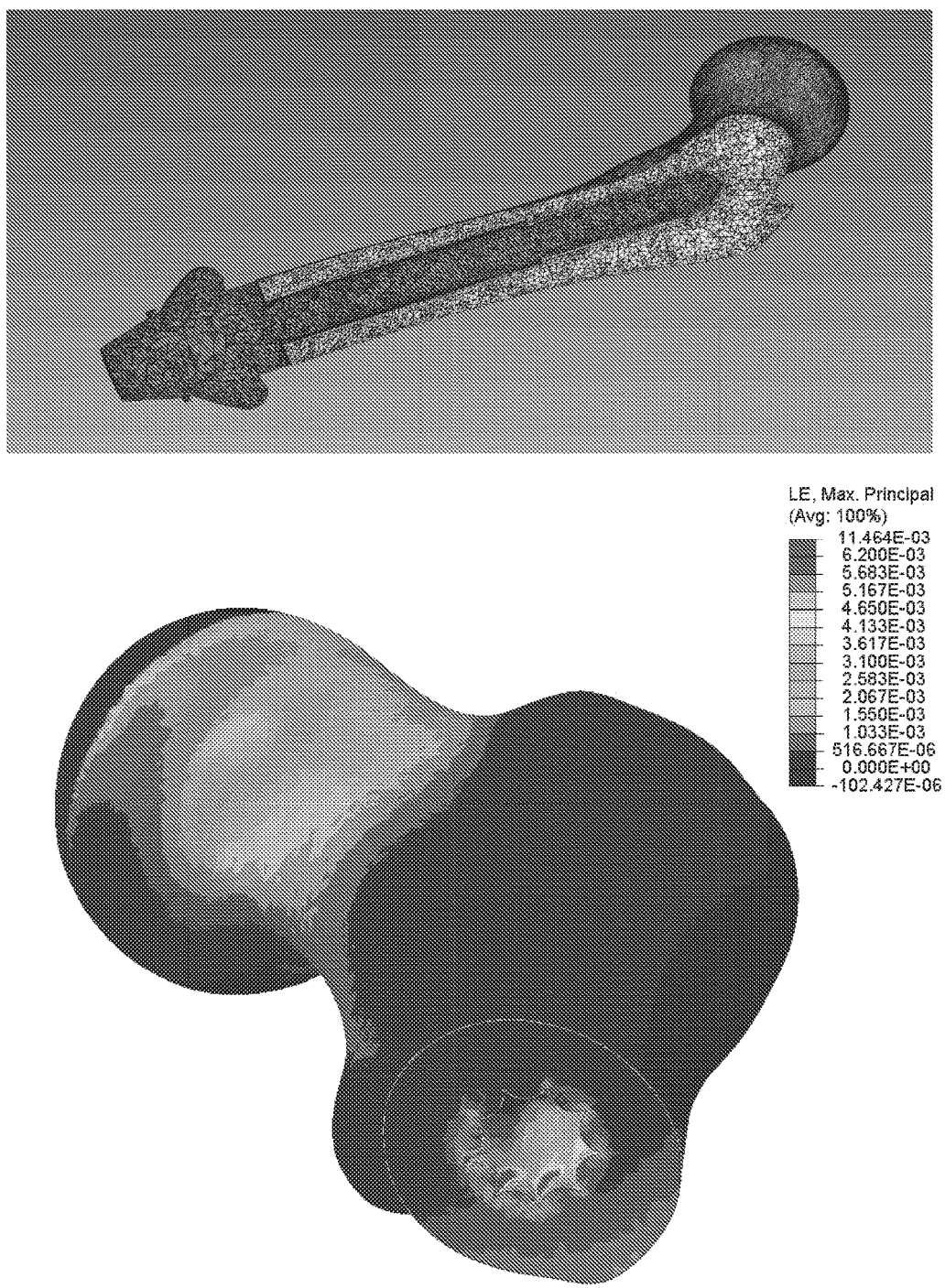
FIG. 19 top panel is a CAD drawing of an implant in a femur (140 mm implant in 190 mm femur) for FEA. The bottom panel is the strain distribution of a FEA experiment for a 140 mm implant having sharp splines in a 250 mm femur.

Further detail of the in silica experiments and methodology is illustrated in FIG. 19. Bone and implant are subject to FEA, including under dangerous loading conditions. One example of a FEA model of a bone with implant is provided in the top panel of FIG. 19, where each element is tetrahedral. Calculated strain and stress in bone under different loading conditions is used to predict potential fracture in bone, based on mechanical properties of bone. FIG. 19 bottom panel shows resultant calculated strain distribution in the femur for an implant with sharp splines. Other FEA is conducted for smooth splines for different implant and femur lengths (see Table 5). Results include the maximum strain that is seen within the bone. Since strain is directly correlated with pain and fracture of the bone, it is one of the most important factors to consider when analyzing the effectiveness of an implant design within bone. The maximum bone strains are provided in Table 5, with one representative strain distribution provided in FIG. 19 (bottom panel). It should be noted that stress within the implant is another important factor, but according to the data, the implant is not exposed to stresses that could cause it to yield; the highest stress observed in the implant for any of the models is below 800 Pa, while Titanium yields at a stress of 880 MPa.

Figure 30:
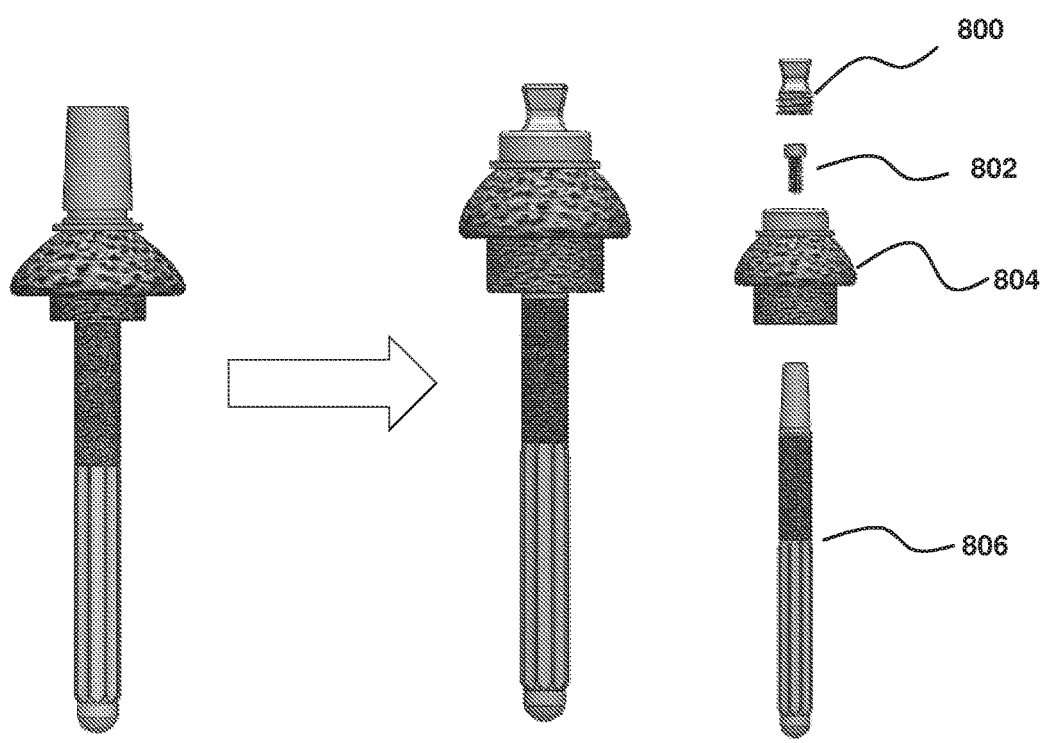
FIG. 30: Comparison between alternative implant configurations, with the right pair of schematics having a pyramid screw and axial taper bolt to connect to an external prosthetic. Common components include a soft tissue cap and stem.
Figure 31:
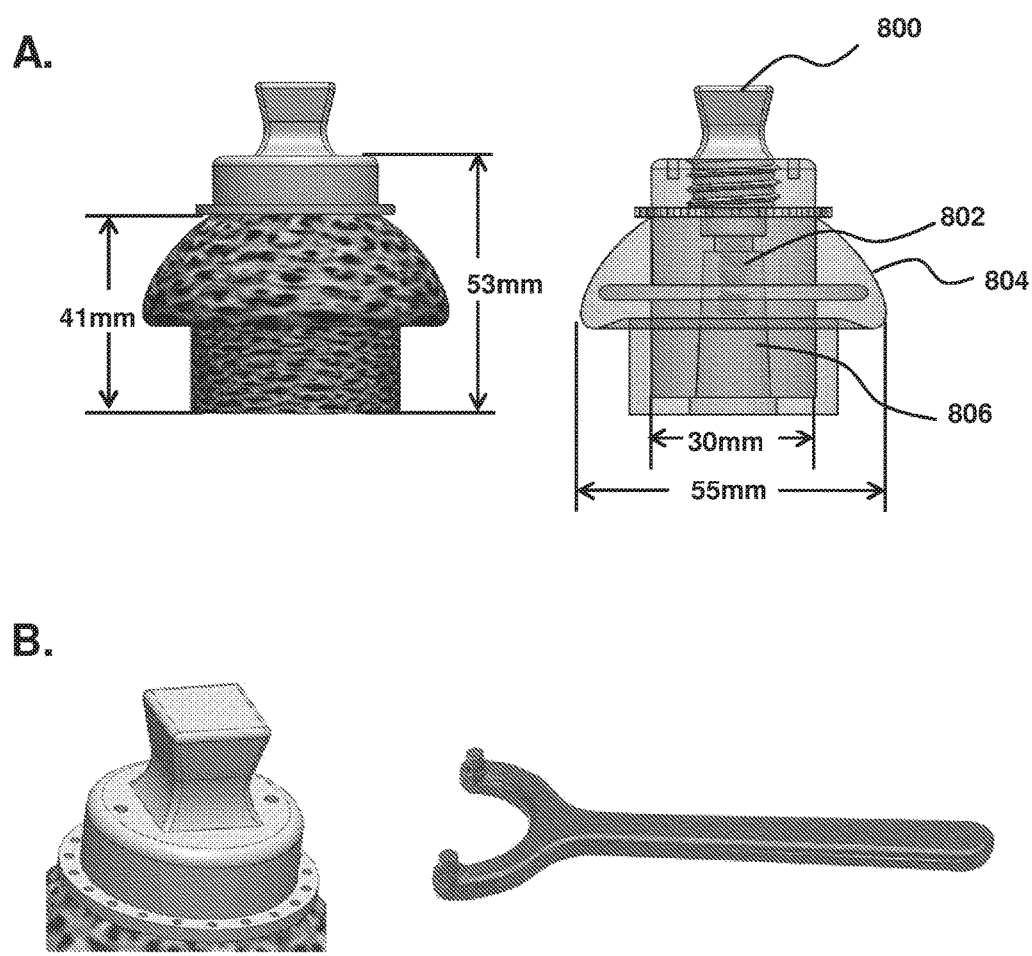
FIG. 31: A. Close-up view of the soft tissue integration portion (part of the prosthetic interface that receives the connector for connection to the prosthetic or failsafe) of the transcutaneous device and exemplary dimensions. B. Top view of the connector received by the prosthetic interface soft tissue integration portion with removal passages to facilitate connection and removal of connector, as desired. The right panel is an example of a wrench that may be employed during connection or removal.

FIGS. 30-31 illustrate another embodiment of a transcutaneous device having a threaded pyramid screw or "connector" 800 for connection to a prosthetic implant (or a failsafe) at one end and the prosthetic interface 804 at the other end. A fastener 802, such as an axial taper bolt, may connect the stem or bone anchor 806 to the prosthetic interface portion 804. FIG. 30 illustrates the different components of a transcutaneous implant connected to each other (top middle panel) and separated from each other (top right panel). A tapered interference fit and axial bolt provide the locking mechanism between the prosthetic interface and bone anchor portions of the implant device. This configuration provides additional connection in the event of wear of the threads of the fastener that could otherwise compromise implant durability. Use of a pyramid shaped connector that attaches to a prosthetic at one end, or a failsafe mechanism element connected thereto, is compatible with a range of prosthetics, including commercially available prosthetics. Such a system permits ease of removal and installation of the prosthetic and failsafe by the patient.

FIG. 31A is a close-up view of the soft tissue ingrowth region of the implant, including the shaped tissue ingrowth surface. The left panel is a solid surface schematic and the right panel is a transparent image to further illustrate the placement of the four components that form the exemplified transcutaneous device. The connector is a pyramid shaped or may have any other shape, depending on the shape of the female connection portion of the prosthetic or the failsafe. The fastener 802 rests beneath the connector 800 for connection to the failsafe mechanism and external prosthesis. Exemplary dimensions are illustrated, and typical taper dimensions may be: 14 mm—large end diameter; 11 mm—small end diameter; 30 mm—length; taper angle—2.87°. The soft tissue integration portion of the prosthetic interface, as illustrated in FIG. 31, operably connects with a fastener and a connector. The connector that is pyramid in shape is advantageous in that it can connect to the failsafe via a plurality of set screws, including the four set screws illustrated in the clamp adapter of FIG. 32. This connection allows for the male exposed end of the connector 800 to be installed and removed easily from either the implant or from the prosthetic or failsafe. This design allows for ready replacement of the connector, such as for use with other prosthetic types or brands, and to replace worn connectors. Optionally, a plurality of receiving passages provide the ability to stabilize the implant while another wrench twists the connector. The plurality of passages may be contained on an exposed surface of the prosthetic interface, such as two passages on opposed sides relative to the connector so that a two prong spanner wrench can stabilize the implant during twisting of the connector by another wrench (FIG. 31B). This ensures that maximum force can be applied to the connector without transferring unduly high forces to the patient or the implant.

The connector that is a pyramid screw can mate with a threaded receptacle of 15 mm in diameter within the body of the prosthetic interface. When the pyramid screw 800 and axial bolt 802 are removed, this threaded receptacle can then be used to remove the prosthetic interface using a push-out screw (distraction bolt). The push-out screw has a step to a smaller diameter at its tip to allow it to fit through the passage for the axial bolt. It can then be used to apply pressure to the end of the male taper of bone anchor 806 to lift the prosthetic interface component off of the stem of the bone anchor 806. The small end of the push-out screw may have a diameter less than 7 mm. This aspect provides unique advantages in the event the implant or part of the implant needs to be removed.

Example 3: Failsafe

Figure 20:
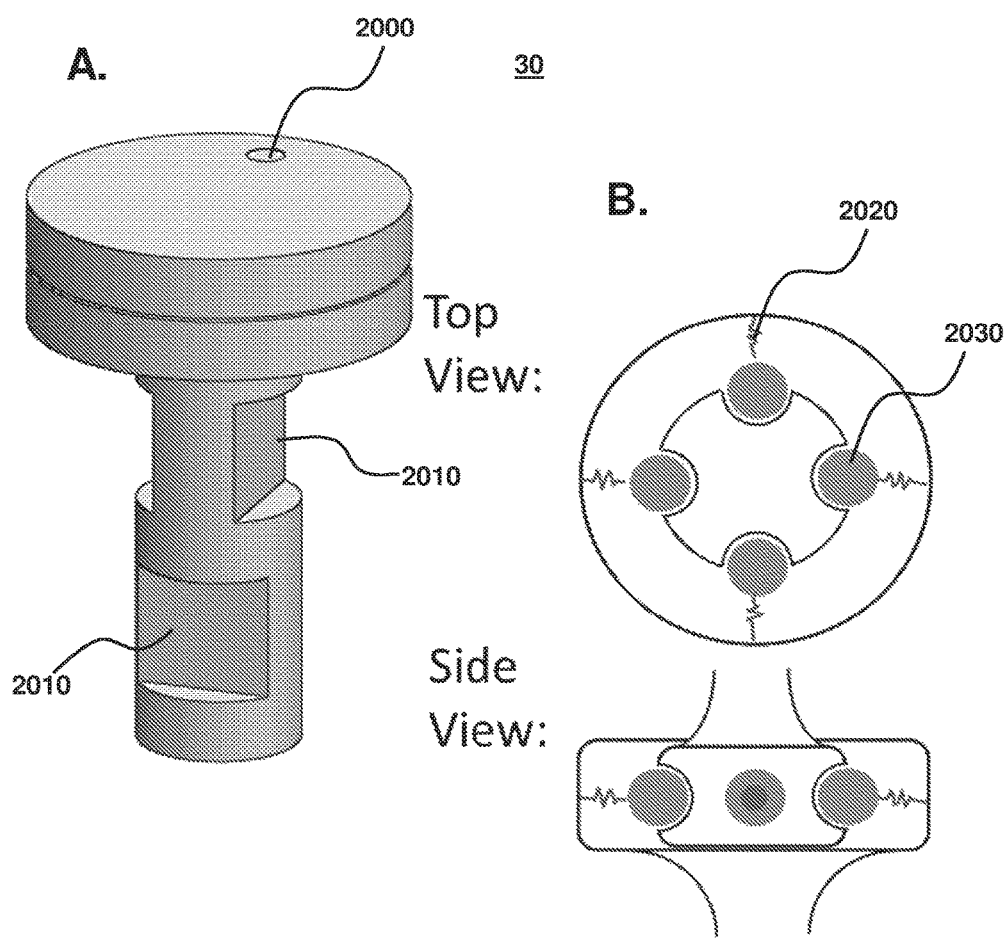
FIG. 20 (A) Failsafe having a shear pin that fails at high torque and controlled breakable material that are notches that fail under high bending force. (B) Failsafe having mechanical springs configured to fail at one or more of high torsion, bending, compression and tension.
Figure 32:
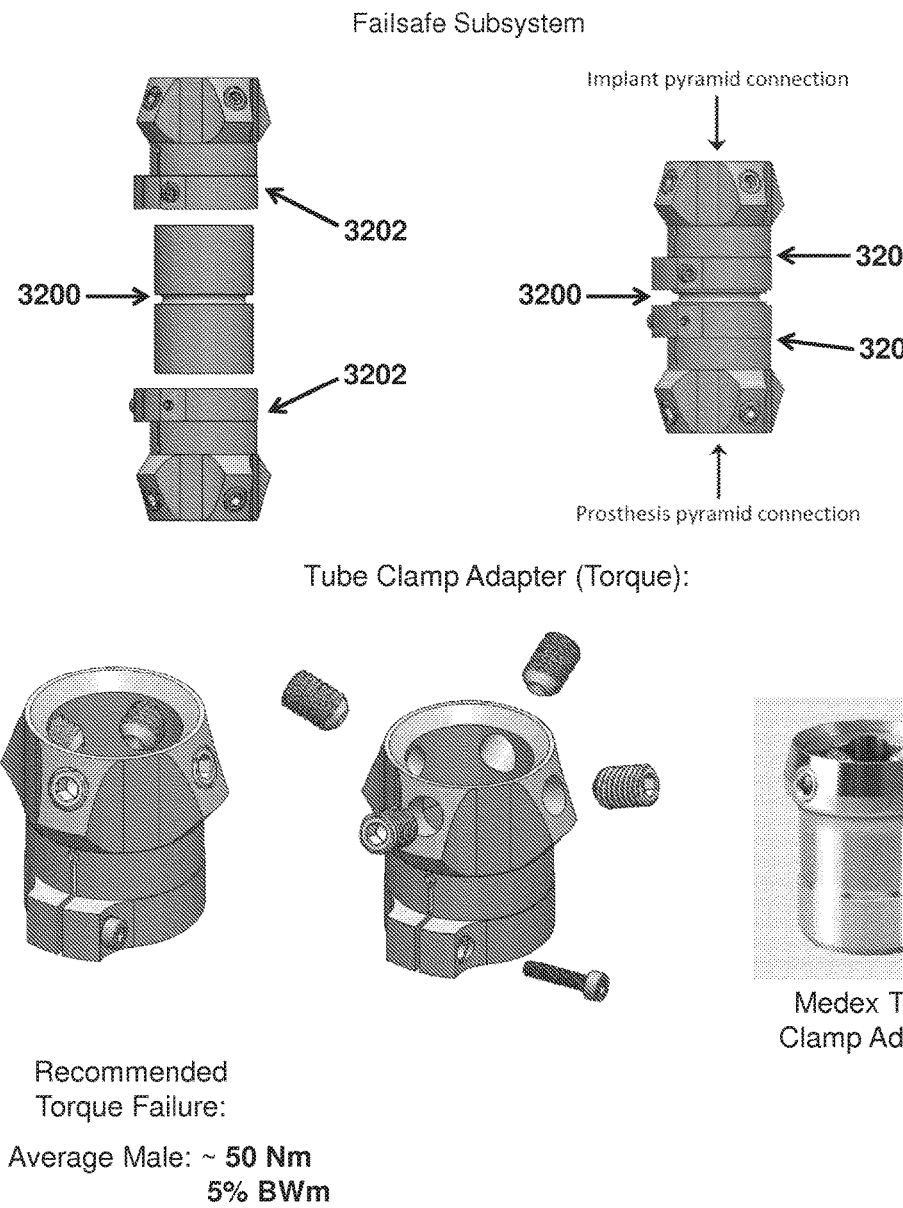
FIG. 32: Alternative failsafe design, for accommodating both bending and torque-induced failure.

Examples of a failsafe 30 (see FIG. 3) for use between the prosthesis and the implant is provided in FIGS. 20 and 32. The failsafe, also referred to as failsafe mechanism or failsafe element, is designed to ensure that dangerous loads are not transmitted to the body, thereby avoiding possible harm such as bone fracture and/or bone anchor damage requiring surgical removal and replacement. Another example is provided in U.S. Pat. Pub. No. 2008/0058957. The implant provided herein may use any failsafe. The failsafe is preferably reliable, simple and easy to use. FIG. 20A shows one option for a failsafe based on controlled material properties, such as a shear pin and two notches. The shear pin 2000 is designed to fail in torsion while the notches 2010 are designed to fail in bending, in this case posterior/anterior and/or medial/lateral directions. Another failsafe option is provided in FIG. 20B that relies on a mechanical system having a plurality of springs 2020 connected to mechanical elements 2030, such as spheres. The springs may be set or adjusted to the desired tension, thereby tailoring failure to a specific individual. For example, older bone may have a lower fracture stress than younger bone. One advantage of the spring-set system of FIG. 20B is that the failsafe may be reset, whereas the failsafe mechanically breaks in FIG. 20A. Other examples of failsafe mechanisms include disk and spring, sphere and spring, and shear pin and shock absorption.

FIG. 32 is another example, with the failsafe comprising a central portion 3200 that is a notched tube to accommodate bending and an end portion 3202 that is a tube clamp adapter for accommodating torque. The notched tube can fail under a bending load and the tube clamp adapter can fail under torque, including under the exemplary torque failure for an average male. Failure load under bending can be accommodated by varying the relative depth of the notch to the tube thickness, with larger notches failing under relative smaller bending loads than smaller notches. The bottom schematics provide examples of tube clamp adaptors that may be used to ensure failure above a certain torque. The bottom right panel is a photograph of a commercial tube claim adapter from Medex International, Inc. (Kensington, Md.). FIG. 32 is an example where the failsafe involves material-controlled failures in bending and torsion. The torque protection is provided by a tube clamp 3202 which may contain four screw receiver and set screws to operably connect to a connector, such as the pyramid connector 800 illustrated in FIG. 32. The torque failure occurs by means of a specified interference fit between the clamp and the internal tube. The torque failure point is selected as desired, such as 50 Nm for an average male. Preferably, the failsafe has a total height that is minimal to limit required resection during surgery. For example, the overall length of the failsafe illustrated in FIG. 32 may be about 40 mm, with an even shorter effective length since the tube and pyramid connector both connect internally.

The bending failure occurs by means of a stress concentration in a failsafe central portion 3200, such as an aluminum (Al 2024-T6) tube (FIG. 32). A hollow tube is preferred in order to lessen the weight of the component. Based on loading determination and average male statistics, failure should occur with a bending moment of 220 Nm. Because the tube is axisymmetric, a bending moment of this magnitude will cause failure of the device in all transverse axes. The full assembly of the failsafe is provided in the top right panel of FIG. 32. In this example, the entire assembled height is about 85 mm, but again, the effective height is less because of the internal pyramid connector connections. The assembled failsafe mechanism provides an important feature to the patient which is the ability for rotational adjustment. This allows the patient to adjust his/her prosthetic to the correct angle with relative ease and simplicity. This is done by loosening the torque screws and rotating the device accordingly and tightening the screws to the specified torque again.

Example 4: Experimental Results for Transcutaneous Implants of Highly Porous Tantalum Porous tantalum has been used in orthopedics for enhanced bone in-growth. The purpose of this example is to evaluate and validate soft tissue integration into transcutaneous porous tantalum implants. Eighteen porous tantalum and four solid titanium implants are placed in the subcutaneous tissues of swine. They are harvested after six weeks and examined microscopically. Epidermal contact, soft tissue penetration, and inflammation are scored for each implant.

Fifteen of sixteen porous implants demonstrate soft and vascular tissue penetration. Nine of sixteen porous implants demonstrate epidermal contact. We use a score of 0-4 to describe tissue ingrowth (0=none and 4=100%). Soft tissue penetration score averages 1.25 at the post and 2.63 at the base of the implant. Vascular penetration score average 1.0 at the post and 2.63 at the base.

Inflammation is evaluated and scored from 0-4 (0=none and 4=marked inflammation). Acute inflammation is present in six of sixteen porous implants with an average score of 1.88 at the post and 0.81 at the base. Chronic inflammation is present in every porous implant with a mean score of 1.5 at the post and 1.56 at the base.

Three of the four solid titanium implants extruded during the study. The one surviving implant does not demonstrate any epidermal contact or tissue ingrowth with chronic and acute inflammation scores of 2 at the base.

Porous tantalum transcutaneous implants experience epidermal, soft tissue, and vascularized tissue integration with minimal inflammation when placed in the subcutaneous tissues of swine. This finding suggests a means for preventing deep infection in transcutaneous implants.

Implantable prosthetic devices have been a mainstay in the treatment of orthopedic problems. Joint replacements are just one example. They have improved the quality of life of millions around the world. The durability and function of these implants are excellent and the complication rates are relatively low (2,8).

Efforts in the development of safe and effective transcutaneous implants however, have not been as successful. Although implantable transcutaneous prosthetics could be of value (for example to the world's amputee population), issues with infection originating at the skin/implant interface that subsequently permeate proximally into the bone/implant interface have precluded their routine use in the general population. Infection rates of up to 18% in healthy selected individuals who have received transcutaneous prostheses have been reported (16, 21, 22).

A number of strategies have been employed and are under current investigation as it relates to prevention of infection at the skin-implant interface with variable results. The use of topical antimicrobials, surface texturing, mechanical stabilization of the skin interface, and surface coatings are reported in the literature (4, 15-19). There have been few reports however, on the use of highly porous tantalum, and what limited reporting that is available is in a non-analagous rabbit skin model (19).

In an attempt to reduce the incidence of deep infection in transcutaneous implants, this example investigates the use of highly porous metal as a soft tissue in-growth medium to help create a 'biologic barrier' against infection at the skin/implant interface. A newer generation of highly porous, open cell 'foam' materials may hold further advantage in creating a vascular environment at the skin/implant interface.

One such technology is highly porous tantalum (Trabecular Metal™ material or TM). This material is relatively inert and can be manufactured up to 80% porosity by volume with open interconnecting dodecahedral shaped cells, allowing for rapid ingrowth of tissues. TM has been used reliably on the bone ingrowth surfaces of orthopedic implants (6,7). An interesting characteristic of highly porous materials is that when the cells are filled with living tissues, the implants become more biologic tissue (80%) than foreign material (20%). The resulting 80% living, vascularized implant should then theoretically hold an advantage against its solid metal counterpart in defending against infection because of this permeating biological tissue acting as both a tight barrier to foreign material as well as providing access to an immune response to actively patrol against foreign material, such as bacteria and virus.

This example evaluates the interaction of the soft tissues and the degree of inflammation present when porous tantalum transcutaneous implants are implanted in the subcutaneous tissues of swine. The porcine model is selected due to the analogous skin structure that swine share with humans. Specifically we ask the questions: Do the soft tissues permeate the porous tantalum implants, and if so to what degree? If so, do we see chronic and acute inflammation in or around the implants in the short term and in what depth patterns? A secondary goal of this study is to evaluate the soft tissue interaction with similarly sized solid titanium implants without porous tantalum material.

The percutaneous porous tantalum implants are expected to demonstrate soft tissue integration with the cutaneous and subcutaneous tissues at the interface providing a stable implant that is infiltrated with biologic materials potentially more resistant to infection. In addition, we expect that the degree of inflammation present should decrease with depth relative to the implant/skin interface because of vascularization that should confine immune response toward the soft-tissue surface interface of the animal.

Figure 21:
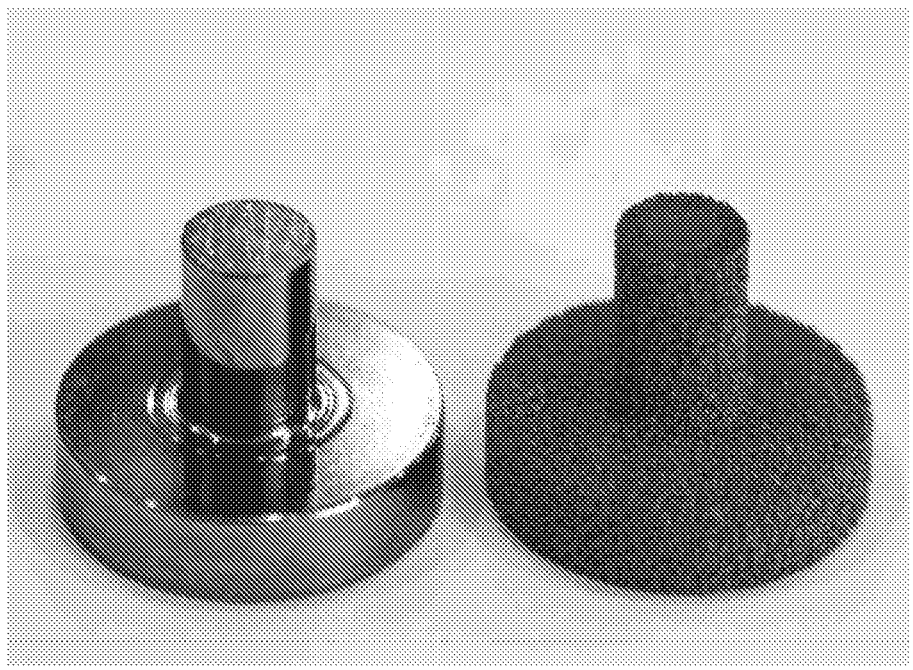
FIG. 21: Photograph of the porous tantalum implant and the solid titanium implant side by side.

MATERIALS AND METHODS: Two groups of implants consisting of 18 porous tantalum implants and 4 solid titanium alloy implants are used. The porous tantalum implants consist of a 10 mm tall by ×9 mm diameter cylindrical percutaneous porous tantalum upright post with a solid 5 mm diameter titanium alloy core atop a 5 mm thick×25 mm diameter discoid porous tantalum base. The structure of the porous tantalum used is 80% porous with dodecahedral interconnecting cells. The average open pore diameter is 450 um. Control implants consisted of polished solid titanium alloy with same outer geometry as the porous tantalum implants (see FIG. 21).

Four domestic female Yorkshire Cross-bread Swine, each at least 12 weeks of age and between 35-45 kg in weight, are used. The animals are continuously housed at the research facility (MPI Research Facility, Mattawan Mich.) and supervised by licensed veterinarians. The animals are each designated as healthy and fit for participation by the supervisory veterinarians upon arrival at the facility.

On day zero of the study, the animals are taken to a sterile operating theater. Each of the animals receive perioperative antibiotics (preoperative dose of Cefazolin followed by 3 doses of IV Ceftiofur post-operatively) and are anesthetized with routine general anesthetics. Once anesthetized, the animals are placed in the prone position and the dorsum of the animals shaved, prepared, and draped in a sterile fashion using Chlorhexadine skin preparation.

A total of 18 porous tantalum implants (6 per animal) are placed in the dorsal subcutaneous tissues of the three test animals designated 802, 804, and 806. Animal 805 receives the 4 solid titanium alloy implants. In each animal, transcutaneous implants are placed at equally spaced intervals parallel to the spine caudal to the level of the scapulae and cranial to the level of the iliac crests. Implants are placed at least 5 cm off the midline and spaced at least 10 cm apart longitudinally.

Figure 23:
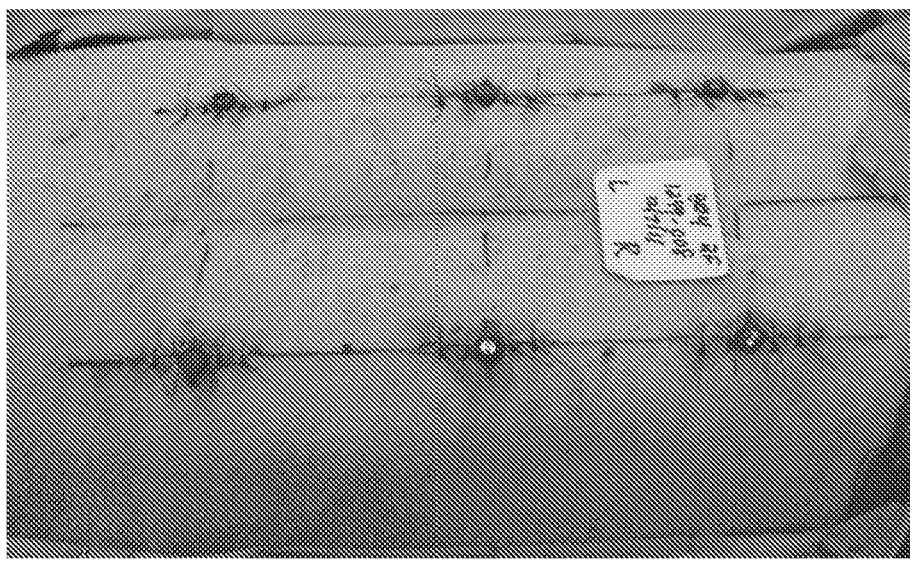
FIG. 23: Photograph of the dorsum of the animal subject after implants have been placed showing the spacing scheme. They are each 5 cm off the midline and placed cephalad to the iliac crest/caudal to the scapulae. Implant centers are spaced apart longitudinally by 10 cm.
Figure 22:
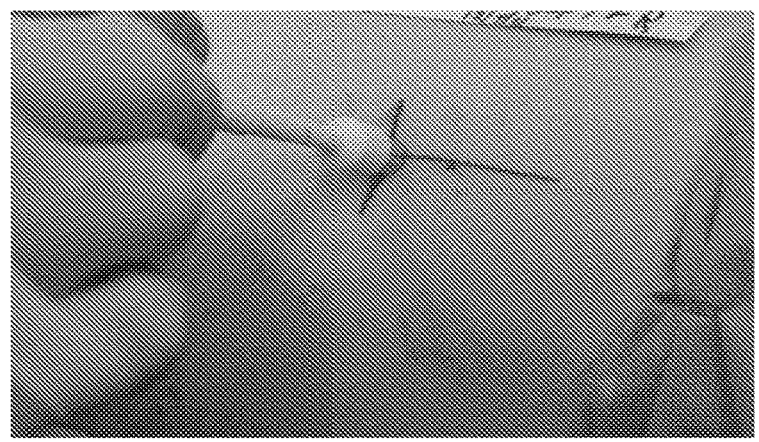
FIG. 22: Photographs of Implant technique: A. a 9 mm dermal punch is used to create a full thickness circular skin defect. B. the circular skin defect is extended using a scalpel 1 cm cephalad and 1 cm caudad. A pocket is then created by bluntly dissecting down to the level of the dorsal muscular fascia. C. Once the pocket is prepared, the implant is placed within the pocket and the edges approximated with nylon sutures.
Figure 22:
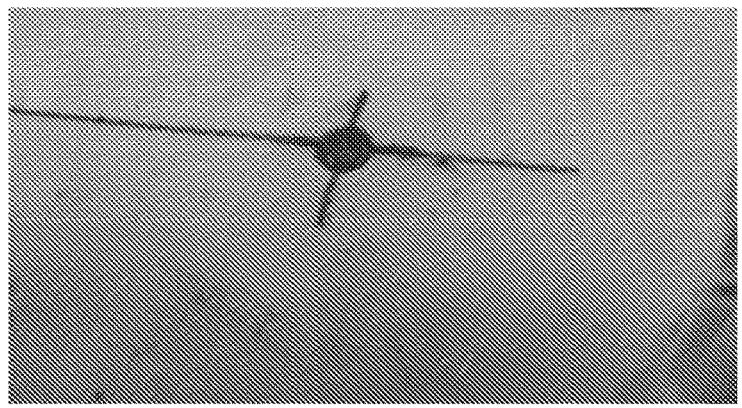
Figure 22:
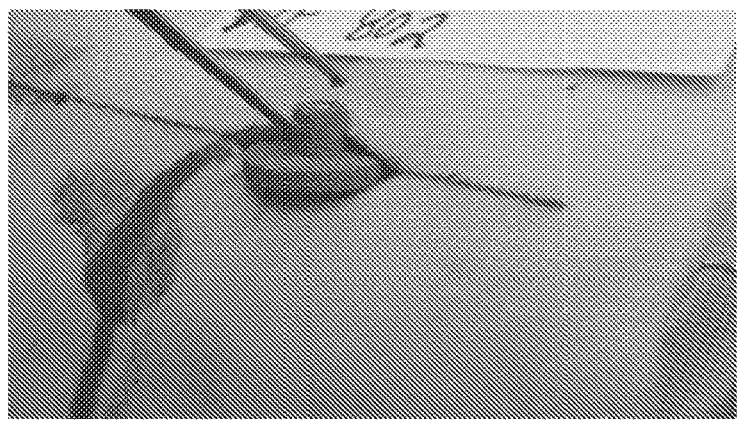
Figure 24:
FIG. 24: Photograph of: A. implanted porous tantalum implant; and B. implanted solid titanium implant.
Figure 24:
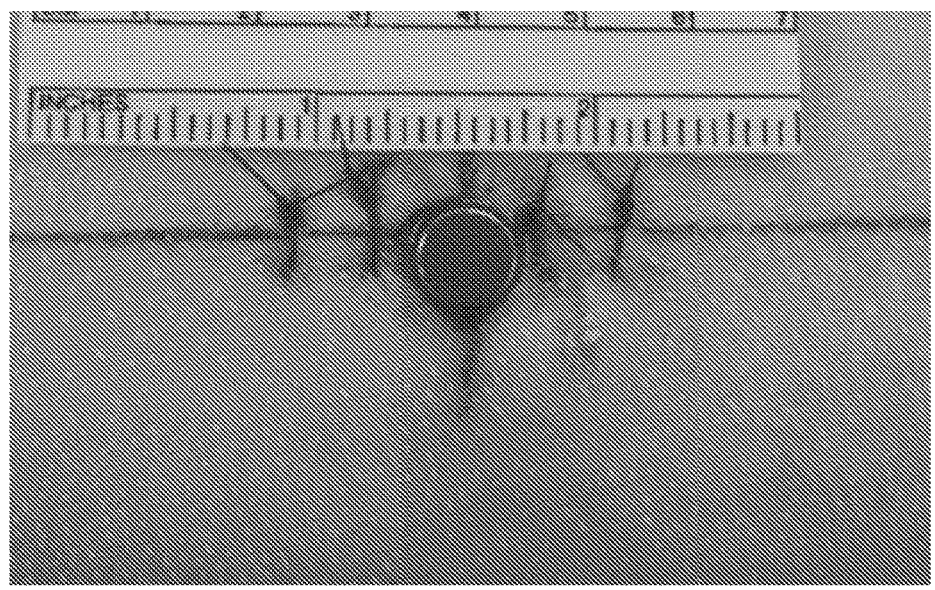

First, a circular defect through the skin is created using a 9 mm dermal punch at each pre-designated implant site to permit transcutaneous penetration of the implant post. Skin incisions are then created extending away from both ends of the circular defect by 1 cm in each direction parallel to the spine. A subcutaneous pocket is created by blunt finger dissection down to the level of the dorsal muscular fascia. The assigned implant is placed into each pocket with the base placed deep abutting the fascia and the post protruding percutaneously (see FIGS. 22-23). Once the implant is positioned, the incision is closed with full thickness nylon sutures to approximate the edges of the longitudinal incision and 'cinch up' the skin against the implant post. The implant sites are dressed in a sterile fashion (see FIG. 24).

Post-operatively, animals are single housed in runs with ample Aspen wood shavings and plexi-glass covering the chain link fencing, to prevent the animals from rubbing the externalized implants against the caging. Post-operative monitoring of the implant sites is conducted through Day 10-14, based on healing at the tissue-implant interface. Implant sites are bandaged Day 0-7 post-operatively with Xenofoam, dry, clean gauze, and VetWrap, or other suitable covering. Discontinuation of dressings is dependent on wound closure and healing around the implant post. Implant sites are cleaned daily. Dirt, debris, and dried exudates are wiped off the implants using clean gauze. Implant sites are then cleaned with chlorhexadine solution. Following cleansing, each implant site is then dried completely with gauze. Implant sites are each photographed weekly.

Figure 25:
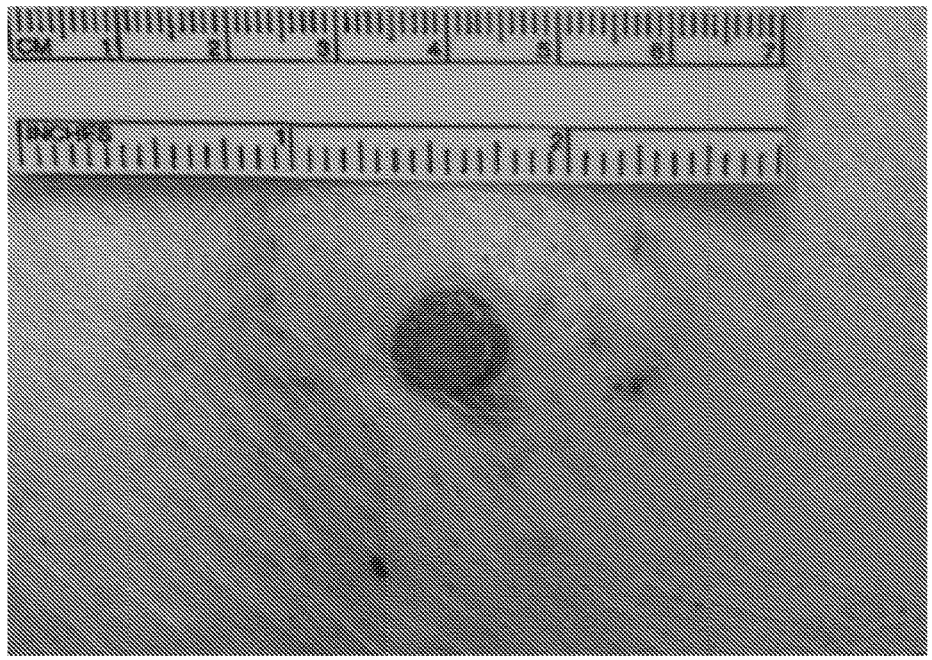
FIG. 25: Photograph of a: A. porous tantalum implant at 42 days; and B. solid titanium implant at 42 days. 3 of the 4 solid implants extruded prior to necropsy.
Figure 25:
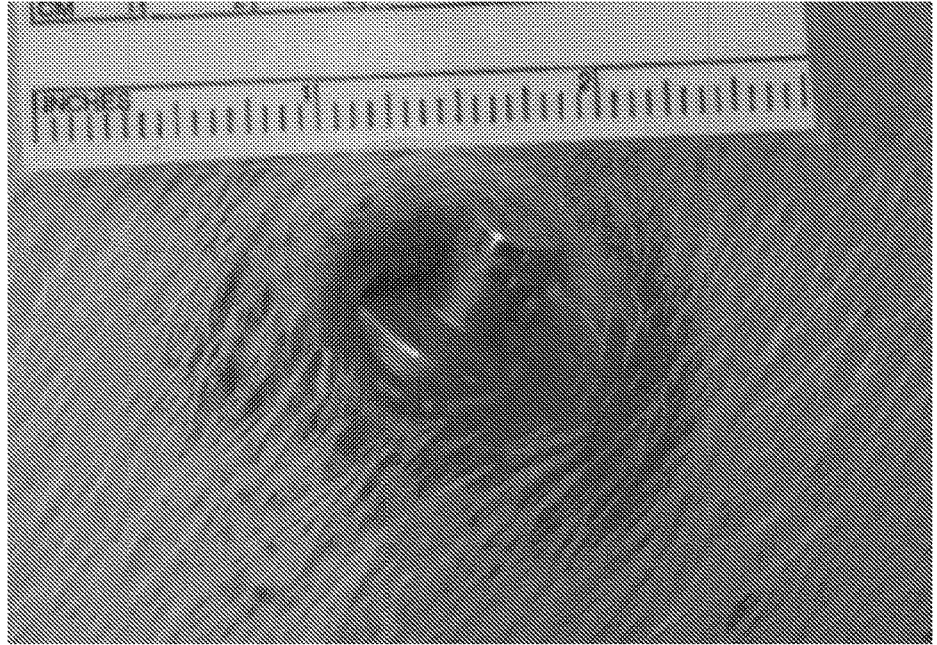

At the termination of the study (Day 42±1), all animals are euthanized and the implant sites (18 porous tantalum implants and 4 solid titanium implants) are photo-documented and excised along with the surrounding soft tissues (see FIG. 25). Each specimen is sectioned through the approximate longitudinal mid-line of the defect site and was embedded in plastic (Technovit 7200 VLC). One ground and polished section is created from each plastic block. All sections are stained with hematoxylin and eosin (H&E) and assessed microscopically for epidermal contact, depth of penetration of soft tissues into the implant, acute and chronic inflammation, and depth of demonstrable vascular invasion by a veterinary pathologist.

Microscopic observation of epidermal contact with the implants is assessed as 0 if no contact is present, 1 if contact was present on one side of the implant post, and 2 if contact is present on both sides of the implant post.

The depth of penetration of soft tissue and vascular tissue at the implant post is assessed using a 'penetration score' of 0-4, where 0=no penetration; 1=penetration of 1-25% of the distance to the titanium post; 2=penetration of 26-50% of the distance to the titanium post; 3=penetration of 51-75% of the distance to the titanium post; and 4=penetration of 76-100% of the distance to the titanium post.

A penetration score is also assigned to each implant at the implant base. The depth of penetration of soft tissue and vascular tissues into the implant base is scored on a scale of 0 to 4. No penetration is given a score of 0; penetration confined to the periphery of the implant is given a score of 1; penetration to the center of the implant is given a score of 4; scores of 2 and 3 denote penetration to areas intermediate to the peripheral and central areas.

Chronic and acute inflammation are assessed and scored at both the post and base portions of the implants. Inflammation is assessed a score of 0-4, where 0=finding not present, 1=minimal, 2=mild, 3=moderate, and 4=marked. Direct observation of bacterial invasion is impossible to assess based on the methods of fixation of the specimens in this study and therefore could not be measured reliably.

Results: All animals survived to study termination. Sixteen of the eighteen porous tantalum implants completely integrated with the surrounding soft tissues and are present in the operative sites at the time of study conclusion. One of the eighteen porous tantalum implants partially extruded and one completely extruded from the operative site Three of the four solid titanium implants completely extruded during the course of the study with only one remaining in situ.

Figure 26:
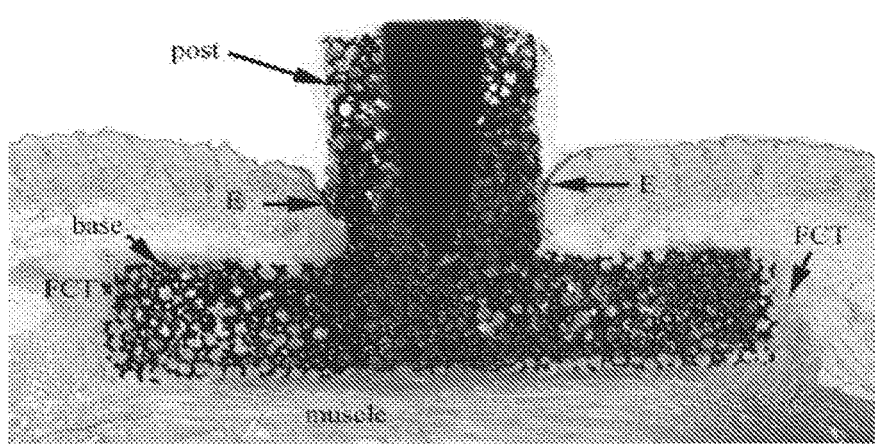
FIG. 26: A. Animal 804, site 4. H&E stain at low power. A typical porous tantalum implant. The epidermis (E) grew up to the trabeculae of the post on both sides but did not penetrate into the pores. Trabecular pores of the base portion of the implant contain vascularized connective tissue or loosely arranged fibrin-like material. There was a mild amount of fibrous connective tissue (FCT) surrounding the implant base, except where portions of the base contacted the underlying muscle. B. Animal 804, site 4. H&E stain at high power (100×). A higher magnification photo at the post/base intersection. This shows epidermal contact with the porous tantalum. C. Animal 806, site 3. H&E stain at high power (100×). A typical cross section near the base/post interface in an in-grown porous tantalum implant. The epidermis is in contact with the deep implant post. Vascularized connective tissue (*) fills the pores of the tantalum implant.
Figure 26:
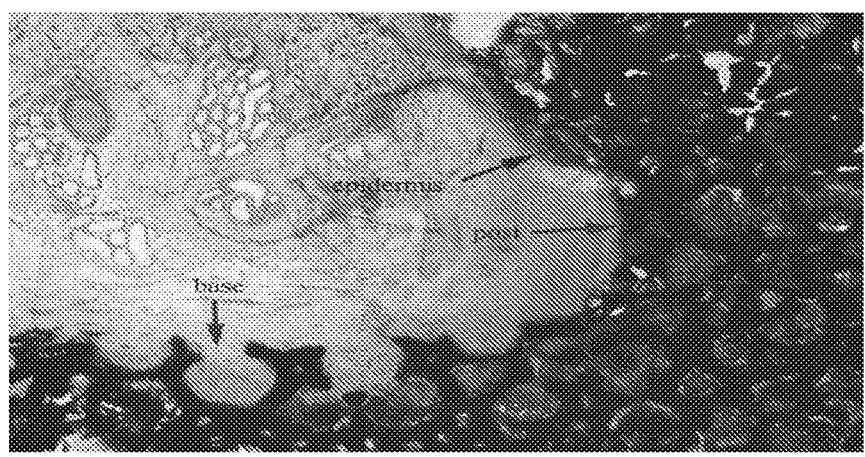
Figure 26:
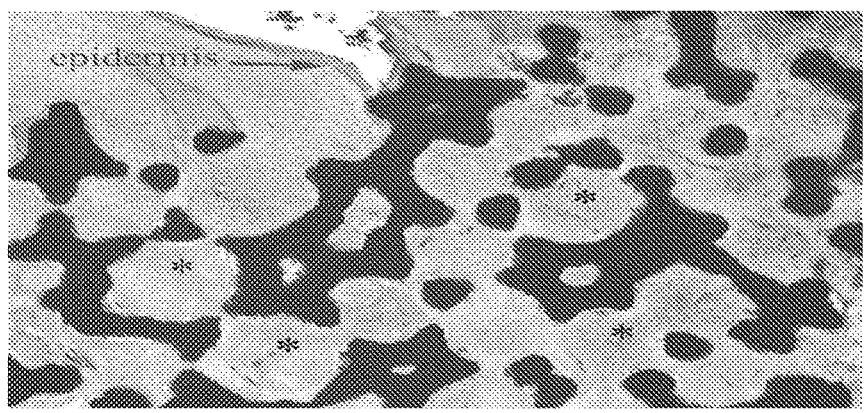
Figure 27:
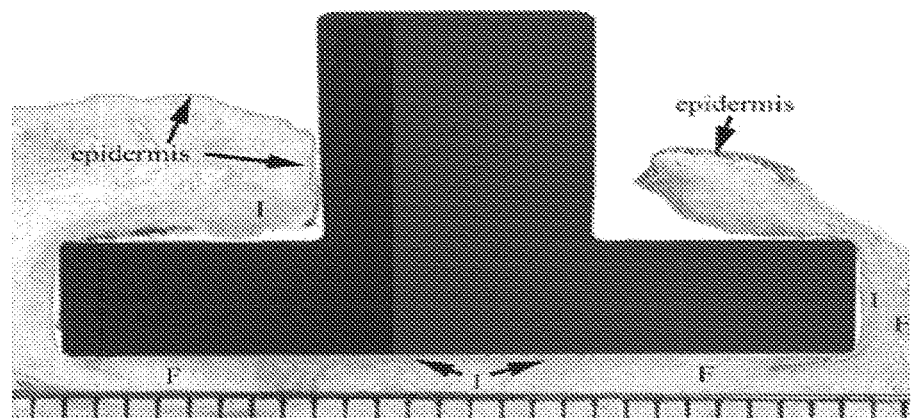
FIG. 27: A. Animal 805, site 1. H&E stain at low power. This is the sole surviving solid titanium implant. The implant is not in direct contact with the epidermis or dermis. The subcutaneous tissue is in contact with the base portion of the implant at the superficial corners and along the deep aspect of the base of the implant. The subcutis contains fibrous connective tissue (F) and mild inflammation (I). B. Animal 805, site 1. H&E stain at high power (100×). A higher magnification photo at the interface between the solid titanium and the surrounding tissues showing accumulation of neutrophils (N) and mononuclear cells (M) in the subcutis adjacent to the base portion of the implant. Note the gap (G) between the implant (IM) and the subcutis.
Figure 27:
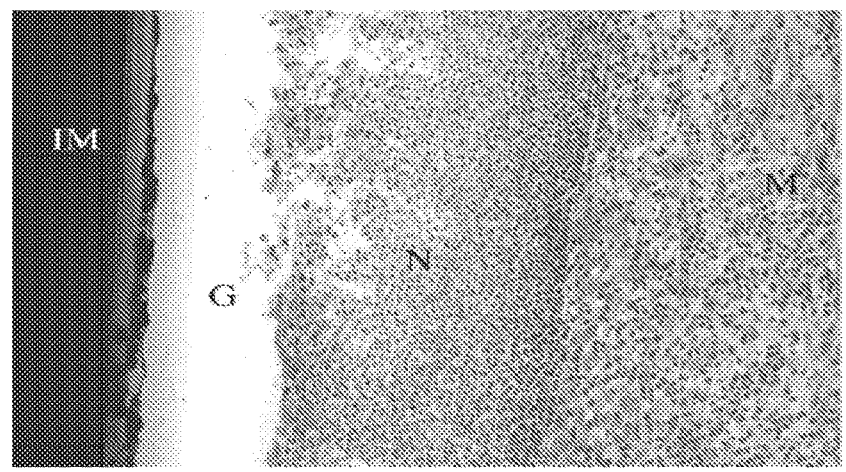

Direct epidermal contact is found to be present in nine of the sixteen porous implants (56%) at the skin/post interface. Of the nine implants in which skin contact is observed, seven exhibited contact with the epidermis on both sides of the implant post while two showed unilateral contact. Each of the implants that did not exhibit direct dermal contact, did exhibit soft tissue ingrowth as described below. At the sites in which epidermis contacted the post, the epidermis grew to the outer edge of the trabeculae, but did not penetrate the pores (see FIG. 26). The only remaining solid titanium implant did not exhibit any dermal contact features microscopically (see FIG. 27).

We assess the degree of soft tissue penetration into the implants. Soft tissues permeate fifteen of the sixteen (94%) porous tantalum implants. This soft tissue in-growth occurred in the post portion of the porous tantalum implant in six of sixteen (38%) implants and in the base portion in fifteen out of sixteen porous tantalum implants (94%). A soft tissue penetration score is assigned to each implant based on the scoring scheme described above. The mean soft tissue penetration score at the porous tantalum post is 1.25 (Range 0-4, STD 1.81) and for tissues permeating the base is 2.63 (Range 0 to 4, STD 1.54). Soft tissue penetration is not seen in the solitary surviving solid titanium implant.

Regarding vascular permeation into the implants, fifteen of sixteen (94%) of the porous tantalum implants exhibit some degree of vascular permeation. The depth of ingrowth is measured using the same penetration score as that for soft tissue ingrowth. Most permeation occurs within the base where 94% of the bases experience vascular ingrowth with a mean score of 2.63 (Range 0 to 4, STD 1.54). Five of the sixteen porous tantalum implants exhibit vascular ingrowth at the post level with a mean penetration score of 1.0 (Range 0 to 4, STD 1.63). There is no vascular permeation present in the sole solid titanium implant examined (see Table 6).

Acute Inflammation (AI) is evaluated in the retrieved implants both at the level of the post and at the level of the base. The degree of AI is scored on a scale from 0-4 as defined above by the observing pathologist. Some degree of AI is found at the post/soft tissue interface in all porous titanium implants with a mean score of 1.88 (Range 0 to 3, STD 0.72). AI is also found in six out of sixteen porous tantalum implant bases (38%) with a mean score of 0.81 (Range 0 to 3, STD 1.22). In the only solid titanium implant, there is no acute inflammation at the post and the acute inflammation present at the base is scored 2.

Chronic inflammation (CI) is scored and recorded in a similar fashion using the same scheme as that for acute inflammation by the observing pathologist. CI is present at the post implant interface in fifteen of sixteen (94%) porous tantalum implants with a mean score of 1.5 (Range 0 to 3, STD 0.73). CI is also present in every base with a mean score of 1.56 (Range 1 to 3, STD 0.81). Chronic inflammation is not seen at the post of the sole solid titanium implant and is scored as a 2 at the base (see Table 7).

Discussion: The development of safe and effective percutaneous implants holds the potential to improve the lives of millions of amputees worldwide. The recent wars in Iraq and Afghanistan have added to the numbers of young, healthy, and previously active amputees. With advances in center of mass protection, battlefield injuries have become more survivable, but have unfortunately yielded more combatants with loss of limb (1,5). Many injured combatants wish to return to active duty and continue the fight despite their injuries.

The predominant method of prosthetic fitting and attachment in amputees has long been the molded socket. Using this method, the residual limb is casted, and a custom molded socket interface is created and placed around the residual limb with a distal attachment point for the external prosthetic device. This technology dates back hundreds of years and (with the exception of changes in materials and techniques) has changed relatively little over that time. This is an expensive and perpetual process over the life of the amputee as their body shape and residual limb go through constant changes (13). While for some patients, this provides an acceptable interface, depending on the location of the amputation and the body type of the individual, socket technology can have its limitations.

As an example, energy transfer is extremely inefficient with the current socket technology—especially in patients with above the knee amputations (AKA). In this subgroup, it takes a single leg amputee up to 50% more energy to perform the same task as a well-bodied individual and up to 250% more energy in double amputees at this level (7,20). This is mostly due to the depth of the soft tissues that typically surrounds the femur and the energy lost in transferring motion from an amputees femur, through these soft tissues, and then on to the prosthetic socket and eventually the prosthesis itself.

Maintaining fit can also be an issue with the amputee population using traditional socket technology. The average individual fluctuates in weight over his adult lifetime by up to 10% (23). Weight fluctuation of this magnitude can make a socket so loose it will fall off or so tight that it creates pressure and skin breakdown. In addition, active amputees who perspire can have difficulty with adherence of their prosthetic sockets. There is also a subgroup of amputees who have skin breakdown issues related to anything from skin conditions to underlying heterotopic bone (6, 10, 14). Each of these issues would become irrelevant if there were a safe, reliable, percutaneous skeletal attachment available to amputees.

Although percutaneous implants have been used for many years in the treatment of amputees in Europe, infection remains an issue (16, 21, 22). Unlike traditional prosthetic devices (such as hip and knee replacements which are implanted completely below the dermal barrier) transcutaneous prostheses, by definition, are exposed to the outside world and the exposed portion inevitably becomes colonized with bacterial flora. When that flora is allowed to migrate along the implant, it eventually infects the bone/implant interface causing deep-seated osteomyelitis and implant loosening.

Various surface coating and texturing strategies have been employed in an effort to reduce the transmigration of bacteria along the implant's skin interface with some success. Puckett et al (18) have demonstrated that nano-texturing the surface of titanium alloy results in increase keratinocyte function (adhesion and spreading). Salinized fibronectin has also been found to promote adhesive surface cell alignment in vivo alone and when combined with hydroxyapatite coatings (4).

Antimicrobials have been investigated as well. The topical antimicrobial ceragenin was applied via an impregnated pad at the skin-implant interface of transcutaneous implants in sheep, but when compared to controls at 24 weeks, there was no advantage relating to prevention of infection (17). Topical 1% pexiganan acetate was applied daily to a percutaneous implant in a rabbit model and was found to reduce incidence of infection by up to 75% when compared to controls at 24 weeks (19).

Other authors have advocated mechanical stabilization of the skin interface as a method to promote skin adhesion and prevent infection. This has led in part to design elements with porous subcutaneous flanges which have been used with success in Europe (9, 15).

A critical element of this example was to demonstrate that soft tissues in and below the skin can effectively integrate themselves into porous tantalum implants. The most effective defense against infection is biologic tissue adhesion and apposition. Biologic tissues have an inherent mechanism to defend against infection: the white blood cell. The vascularity within biologic tissues can also deliver antibiotics (if necessary) to sites of potential infection. By introducing vascularity into the implant, the body's ability to defend against infection at the skin/implant interface is harnessed, creating an effective barrier against deep infection, and increasing the likelihood of successful long-term transcutaneous implant survivability.

This example demonstrates effective, consistent soft tissue and vascular penetration into porous tantalum implants with minimal inflammation in a skin structure model analogous to that of humans. Rather than being encapsulated and extruded as foreign materials usually are, the vast majority of the porous tantalum implants integrated with the tissues, becoming a part of them.

This example focuses on the soft-tissue and vascular interface and so does not address a bone/implant interface. Because there was no bone/implant interface, these implants lacked a stable base and therefore were subjected to small amounts of motion, which may have affected their ability to more fully in-grow. The goal of this example was to focus on the skin-implant interface and prove the viability of this concept before moving on to add other elements such as osseous integration.

We were also unfortunately unable to directly compare the porous tantalum implants to the solid implants due to the fact that three of the four solid implants extruded during the study leaving us only one solid implant to analyze. This made it impossible to provide meaningful statistical comparison. However, we do believe that this further demonstrates the advantage of porous materials over solid materials.

This example confirms that highly porous tantalum implants incorporate with soft tissues at the level of the dermis and subcutis. This finding may be important in improving a transcutaneous implant's ability to resist retrograde migration of bacteria and subsequent infection in the long term. Further studies in an amputee model can provide further understanding of this process when it is coupled with a strong implant/bone base.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a size range, a porosity range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Tables:

TABLE 1

Peak Forces and standard deviations collected from literature involving daily activities presented as their actual and normalized values with respect to mean body weight.

| Reference | Force Units | Mean Peak Forces | | | | | |
|---|---|---|---|---|---|---|---|
| | | $F_{AP}+$ | $F_{AP}-$ | $F_{ML}+$ | $F_{ML}-$ | $F_{IS}+$ | $F_{IS}-$ |
| [10] | Value (N) | 101 | 137 | 93 | x | 769 | x |
| | S.D. (N) | 19 | 98 | 39 | x | 171 | x |
| | Value (% BW) | 12.5 | 16.9 | 11.5 | x | 95.0 | x |
| | S.D. (% BW) | 2.35 | 12.1 | 4.82 | x | 21.1 | x |
| [8] | Value (% BW) | 7.91 | 14.04 | 12.57 | x | 89.32 | x |
| | S.D. (% BW) | 0.123 | 0.051 | 0.072 | x | 0.033 | x |

TABLE 2

Moments and standard deviations collected from literature involving daily activities presented as their actual and normalized values with respect to mean body weight.

| Reference | Moment Units | Mean Peak Moments | | | | | |
|---|---|---|---|---|---|---|---|
| | | $M_{AP}+$ | $M_{AP}-$ | $M_{ML}+$ | $M_{ML}-$ | $M_{IS}+$ | $M_{IS}-$ |
| [10] | Value Nm | 27 | x | 17 | 30 | 5.3 | 6.3 |
| | S.D. (Nm) | 9 | x | 12 | 20 | 3.6 | 2.5 |
| | Value (% BW-m) | 3.34 | x | 2.10 | 3.71 | 0.65 | 0.78 |
| | S.D. (% BW-m) | 1.11 | x | 1.48 | 2.47 | 0.44 | 0.31 |
| [8] | Value (% BW-m) | 2.8 | x | 1.2 | 2.4 | x | x |
| | S.D. (% BW-m) | 9.4 | x | 55.7 | 12.1 | x | x |

TABLE 3

Forces and moments with their respective standard deviations during a forward fall of a transfemoral amputee. Values are presented as their actual and normalized (to body weight) units

| Peak Forces | | | | | | |
|---|---|---|---|---|---|---|
| Force Units | $F_{AP}+$ | $F_{AP}-$ | $F_{ML}+$ | $F_{ML}-$ | $F_{IS}+$ | $F_{IS}-$ |
| Value (N) | 22.73 | 554.13 | 37.71 | 269.63 | 1144.56 | x |
| S.D. (N) | 0 | 0 | 0 | 0 | 0 | x |
| Value (% BW) | 2.49 | 60.77 | 4.14 | 29.57 | 125.52 | x |
| S.D. (% BW) | 0 | 0 | 0 | 0 | 0 | x |

| Peak Moments | | | | | | |
|---|---|---|---|---|---|---|
| Moment Units | $M_{AP}+$ | $M_{AP}-$ | $M_{ML}+$ | $M_{ML}-$ | $M_{IS}+$ | $M_{IS}-$ |
| Vaine Nm | 20.87 | 10.46 | 153.36 | 11.39 | 30.01 | 13.11 |
| S.D. (Nm) | 0 | 0 | 0 | 0 | 0 | 0 |
| Value (% BW-m) | 2.29 | 1.15 | 16.82 | 1.25 | 3.29 | 1.44 |
| S.D. (% BW-m) | 0 | 0 | 0 | 0 | 0 | 0 |

TABLE 4

Summary of quantified loading ranges from literature and HDL data:

| Range | $F_{AP}$ (% BW) | $F_{ML}$ (% BW) | $F_{IS}$ (% BW) | $M_{AP}$ (% BW-m) | $M_{ML}$ (% BW-m) | $M_{IS}$ (% BW-m) |
|---|---|---|---|---|---|---|
| DL Upper Limit | 215 | 86 | 608 | 25 | 136 | 5.8 |

TABLE 5

Maximum bone strains for different implants and bone cuts:

| Implant Length (mm) | Femur Length (mm) | Spline Design | Max Strain |
|---|---|---|---|
| 140 | 190 | Sharp | 15.579e−03 |
| 140 | 190 | Smooth | 10.751e−03 |
| 140 | 250 | Sharp | 11.464e−03 |
| 140 | 250 | Smooth | 8.016e−03 |
| 190 | 250 | Sharp | 4.878e−03 |

TABLE 6

Soft tissue and vascular tissue penetration scores for porous tantalum implants. A measure of penetration to the solid core of the post or the center of the base. 0 = no penetration, 1 = 25% penetration depth, 2 = 50% penetration depth, 3 = 75% penetration depth, 4 = 100% penetration depth. The solid titanium implant did not exhibit any soft tissue or vascular tissue penetration.
Porous Tantalum Implants

| | Soft Tissue Penetration Score | | Vascular Penetration Score | |
|---|---|---|---|---|
| Implant ID | Post Level | Base Level | Post Level | Base Level |
| 802-1 | 4 | 4 | 2 | 4 |
| 802-2 | 0 | 1 | 0 | 1 |
| 802-3 | 0 | 1 | 0 | 1 |
| 802-4 | 0 | 4 | 0 | 4 |
| 802-5 | 0 | 2 | 0 | 2 |
| 802-6 | 0 | 1 | 0 | 1 |
| 804-1 | 4 | 4 | 4 | 4 |
| 804-2 | 4 | 4 | 4 | 4 |
| 804-3 | 4 | 4 | 4 | 4 |
| 804-4 | 0 | 1 | 0 | 1 |
| 804-5 | 0 | 1 | 0 | 1 |
| 804-6 | Extruded | Extruded | Extruded | Extruded |
| 806-1 | Extruded | Extruded | Extruded | Extruded |
| 806-2 | 0 | 4 | 0 | 4 |
| 806-3 | 0 | 4 | 0 | 4 |
| 806-4 | 3 | 4 | 2 | 4 |
| 806-5 | 1 | 3 | 0 | 3 |
| 806-6 | 0 | 0 | 0 | 0 |
| Mean | 1.25 | 2.625 | 1 | 2.625 |
| STD | 1.807 | 1.544 | 1.633 | 1.544 |

TABLE 7

Acute and chronic inflammation scores in the porous tantalum implants. A measure of intensity of inflammation at the stem and base levels.
Microscopic findings in the dermis and subcutis were assessed on a scale of 0-4, where 0 = no inflammation, 1 = minimal inflammation, 2 = mild inflammation, 3 = moderate inflammation, and 4 = marked inflammation.
Porous Tantalum Implants

| | Acute Inflammation Score | | Chronic Inflammation Score | |
|---|---|---|---|---|
| Implant ID | Post Level | Base Level | Post Level | Base Level |
| 802-1 | 2 | 0 | 1 | 1 |
| 802-2 | 3 | 0 | 1 | 1 |
| 802-3 | 2 | 0 | 2 | 1 |
| 802-4 | 2 | 1 | 2 | 1 |
| 802-5 | 1 | 0 | 0 | 1 |
| 802-6 | 3 | 0 | 1 | 1 |
| 804-1 | 1 | 0 | 1 | 1 |
| 804-2 | 2 | 0 | 2 | 1 |
| 804-3 | 2 | 0 | 1 | 2 |
| 804-4 | 1 | 0 | 1 | 1 |
| 804-5 | 1 | 3 | 3 | 3 |
| 804-6 | Extruded | Extruded | Extruded | Extruded |
| 806-1 | Extruded | Extruded | Extruded | Extruded |
| 806-2 | 3 | 3 | 2 | 2 |
| 806-3 | 2 | 0 | 2 | 1 |
| 806-4 | 2 | 1 | 2 | 2 |
| 806-5 | 1 | 2 | 1 | 3 |
| 806-6 | 2 | 3 | 2 | 3 |
| Mean | 1.875 | 0.8125 | 1.5 | 1.5625 |
| STD | 0.719 | 1.223 | 0.730 | 0.814 |

REFERENCES

Examples 1-3

[1] The Limb Loss Research & Statistics Program, "People with Amputation Speak Out," Amputee Coalition of America, Knoxville, Tenn.

[3] N. Fitzpatrick, "An Alternative to limb amputation in dogs and cats", "Society of Practicing Veterinary Surgeons, 2009. [Online]. Available: http://www.fitzpatrick-referrals.co.uk/sites/default/files/ITAP_SPVS_-_article.pdf. [Accessed 5 Sep. 2012].

[4] C. Fryar, G. P and C. Ogden, "Anthropometric reference data for children and adults: United States 2007-2010," National Center for Health Statistics. Vital Health Stat, 2012.

[5] M. A. McDowell, C. D. Fryar, C. L. Ogden and K. M. Flegal, "Anthropometric Reference Data for Children and Adults: United States, 2003-2006," National Health Statistics Reports, no. 10, 2008.

[6] R. Bryan, P. Mohan, A. Hopkins, F. Galloway, M. Taylor and P. Nair, "Statistical Modelling of Whole Human Femur Incorporating Geometric and Materials," Medical Engineering & Physics, pp. 57-65, 25 Jun. 2008.

[7] R. Dumas, L. Cheze and L. Frossard, "Loading applied on prosthetic knee of transfemoral amputee: Comparison of inverse dynamics and direct measurements, Gait & amp; Posture," 2009.

[8] L. Frossard, R. Tranberg, E. Haggstrom, M. Pearcy and R. Brånemark, "Load on osseointegrated fixation of a transfemoral amputee during a fall: loading, descent, impact and recovery analysis," Prosthetics and orthotics international, vol. 34, no. 1, pp. 85-97, 2010.

[9] W. Lee, L. Frossard, K. Hagberg, E. Haggstrom, R. Brånemark, J. Evans and M. Pearcy, "Kinetics of transfemoral amputees with osseiointegrated fixation performing common activities of daily living," Clinical biomechanics, vol. 22, no. 6, pp. 665-673, 2007.

[10] W. Lee, L. a Frossard, K. Hagberg, E. Haggstrom, D. Cow, S. Gray and R. Branemark, "Magnitude and variability of loading on the osseointegrated implant of transfemoral amputees during walking," Medical Engineering & Physics, vol. 30, no. 7, pp. 825-33, 2008.

[11] D. Bozkaya and S. Muftu, "Mechanics of the Tapered Interference Fit in Dental Implants," Journal of Biomechanics, vol. 36, 2003.

[12] "Design Rationale: NexGen Complete Knee Solution," Zimmer.

[13] Zimmer, Trabecular Metal Technology, 2006.

[14] F. Martini, M. Timmons and R. Tallitsh, Human Anatomy, Benjamin Cummings Publishing Company, 2005.

[15] P. Tomaszewski, M. van Diest, S. Bulstra, N. Verdonschot and N. Verkerke, "Numerical analysis of an osseointegrated prosthesis fixation with reduced bone failure risk and periprosthetic bone loss," Journal of Biomechanics, vol. 45, no. 11, pp. 1875-80, 2012.

[16] R. Graven-Nielsen, L. Arendt-Nielsen and S. Mense, "Thermosensitivity of muscle: high-intensity thermal stimulation of muscle tissue induces muscle pain in humans," The Journal of Physiology, vol. 540, no. 2, pp. 647-656, 2002.

REFERENCES

Example 4

1. Belmont P J Jr, McCriskin B J, Sieg R N, Burks R, Schoenfeld A J. Combat wounds in Iraq and Afghanistan from 2005 to 2009. J Trauma Acute Care Surg. 2012; 73(1):3-12.
2. Bjørg-Tilde S Fevang, Stein A Lie, Leif I Havelin, Lars B Engesæter, Ove Fumes. Improved results of primary total hip replacement. Acta Orthop. 2010; 81(6): 649-659.
3. Bobyn J D, Stackpool G J, Hacking S A, Tanzer M, Krygier J J. Characteristics of bone ingrowth and interface mechanics of a new porous tantalum biomaterial. J Bone Joint Surg Br. 1999; 81-B(5): 907-914.
4. Chimutengwende-Gordon M, Pendegrass C, Blunn G. Enhancing the soft tissue seal around intraosseous transcutaneous amputation prostheses using salinized fibronectin titanium alloy. Biomed Mater 2011. 6: 1-11.
5. Gawande A. Casualties of war: military care for the wounded from Iraq and Afghanistan. N Engl J Med 2004; 351:2471-5.
6. Hagberg K, Brånemark R. Consequences of non-vascular trans-femoral amputation: a survey of quality of life, prosthetic use and problems. Prosthet Orthot Int. 2001; 25:186-194.
7. Huang C T, Jackson J R, Moore N B, Fine P R, Kuhlemeier K V, Traugh G H, Saunders P T. Amputation: energy cost of ambulation. Arch Phys Med Rehabil. 1979; 60(1):18-24.
8. Kane R L, Saleh K J, Wilt T J, Bershadsky B. The Functional Outcomes of Total Knee Arthroplasty. J Bone Joint Surg Am. 2005; 87(8):1719-1724.
9. Kang N V, Pendegrass C, Marks L, Blunn G. Osseocutaneous integration of an Intraosseous Transcutaneous Amputation Prosthesis Implant used for reconstruction of a transhumeral amputee: Case Report. J Hand Surg 2010; 35A:1130-1134.
10, Koc E. Tunca M. Akar A, Erbil A H, Demiralp B. Arca E. Skin problems in amputees: a descriptive study. Int J Dermatol. 2008; 47(5):463-6.
11. Levine B, Della Valle C J, Jacobs J J. Applications of Porous Tantalum in Total Hip Arthroplasty. J Am Acad Orthop Surg. 2006; 14 (12): 646-655.
12. Lyon C C, Kulkarni J, Zimerson E, Ross E, Beck M H. Skin disorders in amputees. J Am Acad Dermatol. 2000; 42:501-507.
13. MacKenzie E J, Jones A S, Bosse M J, Castillo R C, Pollak A N, Webb L X, Swiontkowski M F, Kellam J F, Smith D O, Sanders R W, Jones A L, Starr A J, McAndrew M P, Patterson B M, Burgess A R. Health-care costs associated with amputation or reconstruction of a limb-threatening injury. J Bone Joint Surg Am. 2007 August; 89(8):1685-92.
14. Meulenbelt H E, Geertzen J H, Jonkman M F, Dijkstra P U. Skin problems of the stump in lower limb amputees: A clinical study. Acta Derm Venereol. 2011; 91(2):173-7.
15. Pendegrass C J, Goodship A E, Blunn G W. Development of a soft tissue seal around bone anchored transcutaneous amputation prostheses. Biomaterials. 2006; 27: 4183-4191.
16. Pendegrass C J, Gordon D, Middleton C A, Sun S N, Blunn G W. Sealing the skin barrier around transcutaneous implants: in vitro study of keratinocyte proliferation and adhesion in response to surface modifications of titanium alloy. J Bone Joint Surg Br. 2008; 90(1):114-21.
17. Perry E L, Beck P J, Williams D L, Bloebaum R D. Assessing pen-implant tissue infection prevention in a percutaneous model. J Biomed Mat. Part B 2009; 397-408.
18. Puckett S D, Lee P L, Ciombor D M. Aaron R K, Webster T J. Nanotextured titanium surfaces for enhancing skin growth on transcutaneous Osseointegrated devices. Acta Biomaterialia. 2010; 6: 2352-2362.
19, Rosenbaum Chou T G, Petti C A, Szakacs J, Bloebaum R D. Evaluating antimicrobials and implant materials for infection prevention around transcutaneous Osseointegrated implants in rabbit model. J Biomed Mat. Part A 2009; 942-952.
20. Rowe D A, McMinn D, Peacock L, Buis A W P, Sutherland R, Henderson E, Hewitt A. Cadence. Energy Expenditure and Gait Symmetry During Music-Prompted and Self-Regulated Walking in Adults with Unilateral Transtibial Amputation. J Phys Act Health. 2013 Jan. 30. [epub ahead of print]
21. Sullivan, Uden M, Robinson K P. Rehabilitation of the Trans-Femoral amputee with an osseointegrated prosthesis: the United Kingdom experience. Orthotics International. 2003; 27: 114-20.
22. Tillander J, Hagberg K, Hagberg L, Branemark R. Osseointegrated titanium implants for limb prostheses attachments. Clin Orthop Relat Res. 2010; 468: 2781-2788.
23. Williamson D F. Descriptive epidemiology of body weight and weight change in U.S. adults. Ann Intern Med. 1993; 119:646-649

I claim:

1. A transcutaneous device to anchor an external prosthetic device to a bone, the transcutaneous device comprising:
a bone anchor implantable into bone and including a male end configured to extend from the bone, wherein the male end has a threaded passage for receiving a fastener, the passage configured to extend along a longitudinal length of the male end external to the bone;
a prosthetic interface configured for implantation external to the bone and configured for soft tissue ingrowth and vascularization after implantation, the prosthetic interface having a male connection configured to extend external to the soft tissue and configured to mate with the external prosthetic device, the prosthetic interface having a female connection configured to receive the male end of the bone anchor therein, wherein the prosthetic interface has a through bore that extends longitudinally from the male connection to the female connection, and wherein the threaded passage and the through bore are substantially aligned to receive the fastener to couple the prosthetic interface to the bone anchor when the male end of the bone anchor is received in the female connection of the prosthetic interface; and
a failsafe comprising a proximal portion and a distal portion, the proximal portion couplable to the prosthetic interface external to the bone and the soft tissue at a proximal end, and couplable to the external prosthetic device at a distal end, wherein the failsafe includes a shear pin connecting the proximal portion and the distal portion, the shear pin configured to separate the proximal portion from the distal portion to separate the prosthetic device from the prosthetic interface when a predetermined shear load is applied to the failsafe, wherein a shaft of the failsafe includes a medial/lateral bending notch configured to separate the prosthetic device from the prosthetic interface when a predetermined medial/lateral bending load is applied to at least one of the proximal portion and the distal portion, and wherein the failsafe includes an anterior/posterior bending notch configured to separate the prosthetic device from the prosthetic interface when a predetermined anterior/posterior bending load is applied to the failsafe.

2. The transcutaneous device of claim 1, wherein the male end of the bone anchor is received in the female connection so as to be inaccessible from external to the soft tissue and the bone when the fastener couples the prosthetic interface to the bone anchor.

3. The transcutaneous device of claim 1, wherein the fastener is configured to reversibly secure the prosthetic interface to the bone anchor and is removable from the bone anchor and the male connection of the prosthetic interface external to the soft tissue and the bone.

4. The transcutaneous device of claim 1, wherein the bone anchor is configured to be accessible by removing the fastener from the bone anchor and the prosthetic interface and then by removing the prosthetic interface from the bone anchor.

5. The transcutaneous device of claim 1, wherein the fastener comprises a bolt that is reversibly connected to the bone anchor, wherein threads on the bolt and the threaded passage allow the bolt to be removed from the bone anchor and the through bore of the prosthetic interface allows the fastener to be removed from the prosthetic interface to allow for decoupling and removal of the prosthetic interface from the bone anchor.

6. The transcutaneous device of claim 1, wherein the fastener comprises a distraction bolt configured to provide an extraction force for facilitating removal of the prosthetic interface from the soft tissue.

7. The transcutaneous device of claim 1, wherein the male end of the bone anchor is tapered and the female connection of the prosthetic interface is similarly tapered to create a press-fit connection between the prosthetic interface and the bone anchor when the male end of the bone anchor is received in the female connection of the prosthetic interface.

8. The transcutaneous device of claim 1, wherein the male end of the bone anchor and the female connection of the prosthetic interface are configured to create a press-fit connection between the prosthetic interface and the bone anchor when the male end of the bone anchor is received in the female connection of the prosthetic interface.

9. The transcutaneous device of claim 1, wherein the prosthetic interface has a bulbous portion with a shaped tissue ingrowth surface proximal of the male connection, wherein the shaped tissue ingrowth surface is configured for soft tissue ingrowth and vascularization after implantation and the male connection extends less than half a longitudinal length of the bone anchor.

10. The transcutaneous device of claim 9, wherein the shaped tissue ingrowth surface comprises:
an apex region concentrically positioned on a distal portion of a central body outer surface;
a rounded radial edge portion; and
a convex outer-facing surface extending between the apex region and the rounded radial edge portion.

11. The transcutaneous device of claim 10, wherein the prosthetic interface includes a ring configured to mechanically stabilize the shaped tissue ingrowth surface.

12. The transcutaneous device of claim 10, wherein the prosthetic interface includes a suture ring positioned at the apex region of the shaped tissue ingrowth surface to provide an anchoring point for skin upon implantation.

13. A transcutaneous device to anchor an external prosthetic device to a bone, the transcutaneous device comprising:
a bone anchor implantable into bone and including a tapered male end configured to extend from a bone ingrowth portion and from the bone;
a prosthetic interface configured for implantation external to bone and configured for soft tissue ingrowth and vascularization after implantation, the prosthetic interface having a male connection configured to extend external to the soft tissue and configured to mate with the external prosthetic device, the prosthetic interface having a tapered female connection configured to receive the tapered male end of the bone anchor therein to create a press-fit connection between the prosthetic interface and the bone anchor external to the soft tissue; and
a failsafe comprising a proximal portion couplable to the prosthetic interface external to the bone and the soft tissue at a proximal end of the proximal portion, the proximal portion couplable to the external prosthetic device at a distal end of the proximal portion, wherein the failsafe includes a distal portion and a shear pin connecting the proximal portion and the distal portion, the shear pin configured to separate the prosthetic device from the prosthetic interface when a predetermined shear load is applied to the failsafe, wherein a shaft of the failsafe includes a first bending notch configured to mechanically break to separate the prosthetic device from the prosthetic interface when a predetermined first bending load is applied to the failsafe, and wherein the failsafe includes a second bending notch configured to separate the prosthetic device from the prosthetic interface when a predetermined second bending load is applied to the failsafe.

14. The transcutaneous device of claim 13, wherein the male end of the bone anchor is received in the female connection so as to be inaccessible from external to the soft tissue and the bone when the prosthetic interface is connected the bone anchor.

15. The transcutaneous device of claim 1, wherein:
the male end has a threaded passage for receiving a fastener, the passage extending along a longitudinal length of the male end; and
the prosthetic interface has a through bore that extends longitudinally from the male connection to the female connection, and wherein the threaded passage and the through bore are substantially aligned to receive the fastener to couple the prosthetic interface to the bone anchor when the male end of the bone anchor is received in the female connection of the prosthetic interface.

16. The transcutaneous device of claim 15, wherein the fastener is configured to reversibly secure the prosthetic interface to the bone anchor and is removable from the bone anchor and the male connection of the prosthetic interface external to the soft tissue and the bone.

17. The transcutaneous device of claim 15, wherein the bone anchor is configured to be accessible by removing the fastener from the bone anchor and the prosthetic interface and by removing the prosthetic interface from the bone anchor.

18. The transcutaneous device of claim 15, wherein the fastener comprises a bolt that is reversibly connected to the bone anchor, wherein threads on the bolt and the threaded passage allow the bolt to be removed from the bone anchor and the through bore of the prosthetic interface allows for removal of the fastener from the prosthetic interface to allow for decoupling and removal of the prosthetic interface from the bone anchor.

19. The transcutaneous device of claim 15, wherein the fastener comprises a distraction bolt configured to provide an extraction force for facilitating removal of the prosthetic interface from the soft tissue.

20. A transcutaneous device to anchor an external prosthetic device to a bone, the transcutaneous device comprising:
a bone anchor implantable into bone and including a tapered male end configured to extend from the bone; and
a prosthetic interface configured for implantation external to bone and configured for soft tissue ingrowth and vascularization after implantation, the prosthetic interface having a male connection configured to extend external to the soft tissue and configured to mate with the external prosthetic device, the prosthetic interface having a tapered female connection configured to receive the tapered male end of the bone anchor therein to create a press-fit connection between the prosthetic interface and the bone anchor; and
a failsafe comprising a proximal portion and a distal portion, the proximal portion couplable to the prosthetic interface external to the bone and the soft tissue at a proximal end, and couplable to the external prosthetic device at a distal end, wherein the failsafe includes a shear pin connecting the proximal portion and the distal portion, the shear pin configured to separate the proximal portion from the distal portion to separate the prosthetic device from the prosthetic interface when a predetermined shear load is applied to at least one of the proximal portion and the distal portion, wherein a shaft of the failsafe includes a medial/lateral bending notch configured to mechanically break to separate the prosthetic device from the prosthetic interface when a predetermined medial/lateral bending load is applied to the failsafe, and wherein the failsafe includes an anterior/posterior bending notch configured to separate the prosthetic device from the prosthetic interface when a predetermined anterior/posterior bending load is applied to the failsafe.

* * * * *

UNITED STATES PATENT AND TRADEMARK OFFICE
CERTIFICATE OF CORRECTION

PATENT NO. : 10,390,975 B2
APPLICATION NO. : 15/241180
DATED : August 27, 2019
INVENTOR(S) : Ronald Hugate Page 1 of 1

It is certified that error appears in the above-identified patent and that said Letters Patent is hereby corrected as shown below:

In the Claims

In Column 35, Line 14, in Claim 15, delete "claim 1," and insert --claim 13,-- therefor Signed and Sealed this
Fifth Day of May, 2020

Andrei Iancu
*Director of the United States Patent and Trademark Office*